(12) United States Patent
Ponce et al.

(10) Patent No.: US 11,793,592 B2
(45) Date of Patent: Oct. 24, 2023

(54) SYSTEMS AND METHODS FOR A STEREOTACTIC COORDINATE ADJUSTER

(71) Applicant: Dignity Health, San Francisco, CA (US)

(72) Inventors: Francisco Ponce, San Francisco, CA (US); Baltazar Zavala, San Francisco, CA (US); Dakota Graham, San Francisco, CA (US)

(73) Assignee: Dignity Health, San Francisco, CA (US)

( * ) Notice: Subject to any disclaimer, the term of this patent is extended or adjusted under 35 U.S.C. 154(b) by 0 days.

(21) Appl. No.: 17/905,314

(22) PCT Filed: Mar. 5, 2021

(86) PCT No.: PCT/US2021/021163
§ 371 (c)(1),
(2) Date: Aug. 30, 2022

(87) PCT Pub. No.: WO2021/178856
PCT Pub. Date: Sep. 10, 2021

(65) Prior Publication Data
US 2023/0126264 A1   Apr. 27, 2023

Related U.S. Application Data

(60) Provisional application No. 62/985,510, filed on Mar. 5, 2020.

(51) Int. Cl.
*A61B 90/10*   (2016.01)

(52) U.S. Cl.
CPC .................................. *A61B 90/10* (2016.02)

(58) Field of Classification Search
CPC ......... A61B 90/10; A61B 90/11; A61B 90/14; A61B 90/39; A61B 2090/067; A61B 2090/101; A61B 2090/103; A61B 2090/3983; A61B 34/20; A61B 2034/2068
See application file for complete search history.

(56) References Cited

U.S. PATENT DOCUMENTS

| | | |
|---|---|---|
| 4,608,977 A | 9/1986 | Brown |
| 5,143,076 A | 9/1992 | Hardy et al. |
| 6,080,164 A | 6/2000 | Oshio et al. |
| 7,794,469 B2 | 9/2010 | Kao et al. |
| 2021/0038338 A1 | 2/2021 | Lee et al. |

OTHER PUBLICATIONS

Patent Cooperation Treaty, International Search Report and Written Opinion, International Application No. PCT/US2021/021163, dated May 20, 2021, 11 pages.

*Primary Examiner* — Robert A Lynch
(74) *Attorney, Agent, or Firm* — Polsinelli PC

(57) ABSTRACT

Various embodiments of a stereotactic coordinate adjuster system and associated method for positional adjustment of components of a stereotactic system are disclosed herein. The system provides fine adjustment to the stereotactic system by providing form-fitting components that encapsulate components of the stereotactic system and allow for fine positional adjustment of an arc support member and a slide portion of the stereotactic system.

32 Claims, 19 Drawing Sheets

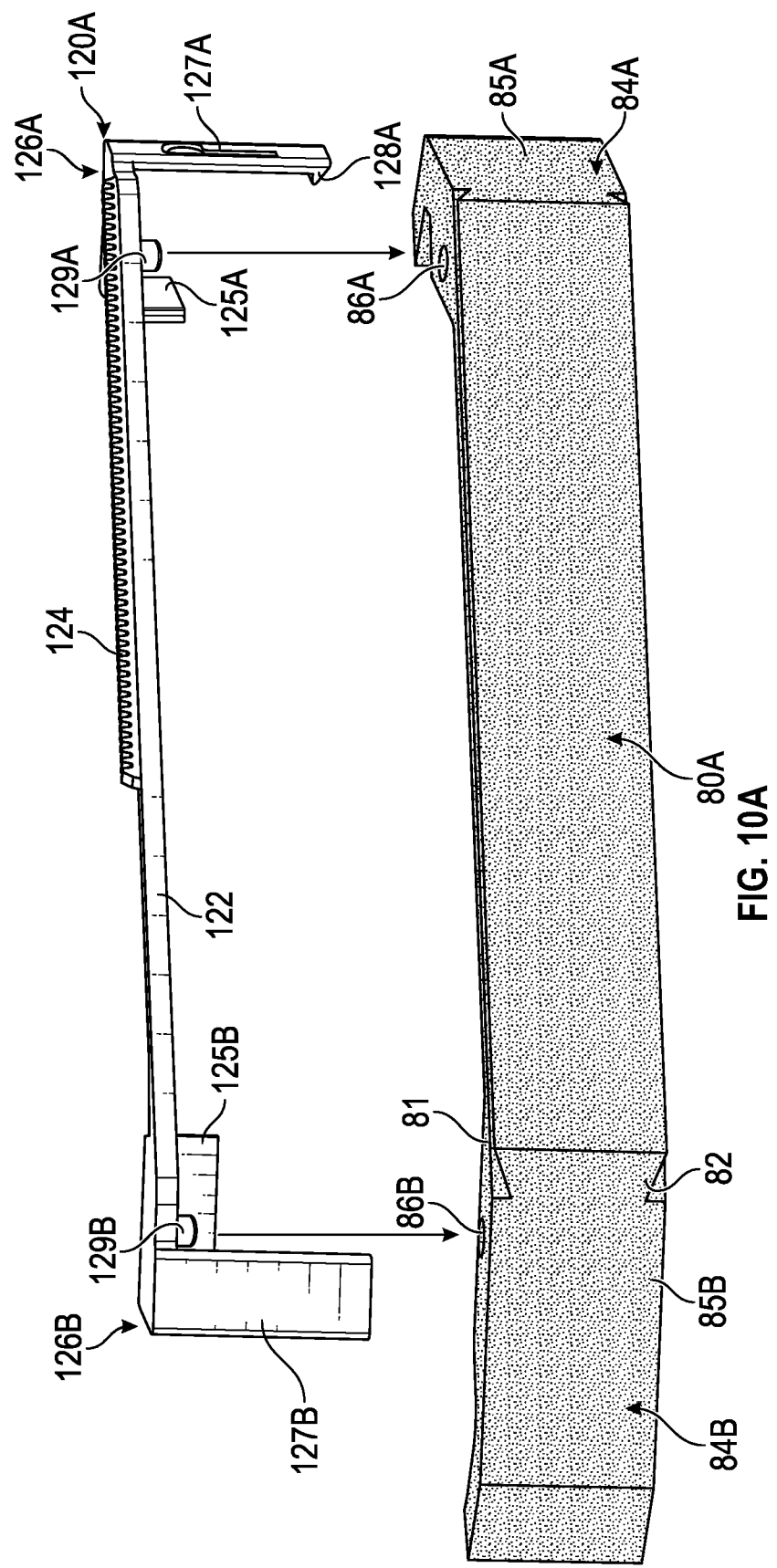

SYSTEMS AND METHODS FOR A STEREOTACTIC COORDINATE ADJUSTER

FIELD

The present disclosure generally relates to stereotactic surgical frames, and in particular, to a system and associated method for a stereotactic coordinate adjuster for use with a surgical frame for improved positional precision in surgical applications.

BACKGROUND

In functional neurosurgery, among other applications, the use of stereotactic instruments to navigate and localize areas of the body with precision is key to ensuring success. In particular, deep brain stimulation (DBS) surgery has provided symptomatic relief to tens of thousands of patients suffering from movement disorders. DBS surgery involves the permanent placement of an electrode wire in very precise areas deep inside the brain. To achieve this, a device known as the Leksell frame is used to place the DBS electrodes at the appropriate target with millimeter precision.

Currently, the use of the Leksell frame involves very tedious manual adjustments to metal scales that set X, Y, and Z coordinates of the frame. Due to the rugged nature of the frame (designed in the 1940s), as well as a working space involving sterile and non-sterile areas of the operative field, adjusting the frame is a time-consuming and frustrating process that must be performed multiple times during DBS surgery. Simultaneously positioning multiple positioning variables on the Leksell frame can lead to imprecision, which is detrimental to the millimeters precision required in DBS surgery. Given that both time and accuracy are of the essence for a successful DBS surgery, adjustment of the Leksell frame presents a problem that is ripe for improvement and innovation.

It is with these observations in mind, among others, that various aspects of the present disclosure were conceived and developed.

BRIEF DESCRIPTION OF THE DRAWINGS

FIG. 10A is a first view in a series of views showing the Y-rack of FIG. 9A being engaged with a frame portion of the Leksell frame of FIGS. 1A and 1B;

Corresponding reference characters indicate corresponding elements among the view of the drawings. The headings used in the figures do not limit the scope of the claims.

DETAILED DESCRIPTION

Figure 1A:
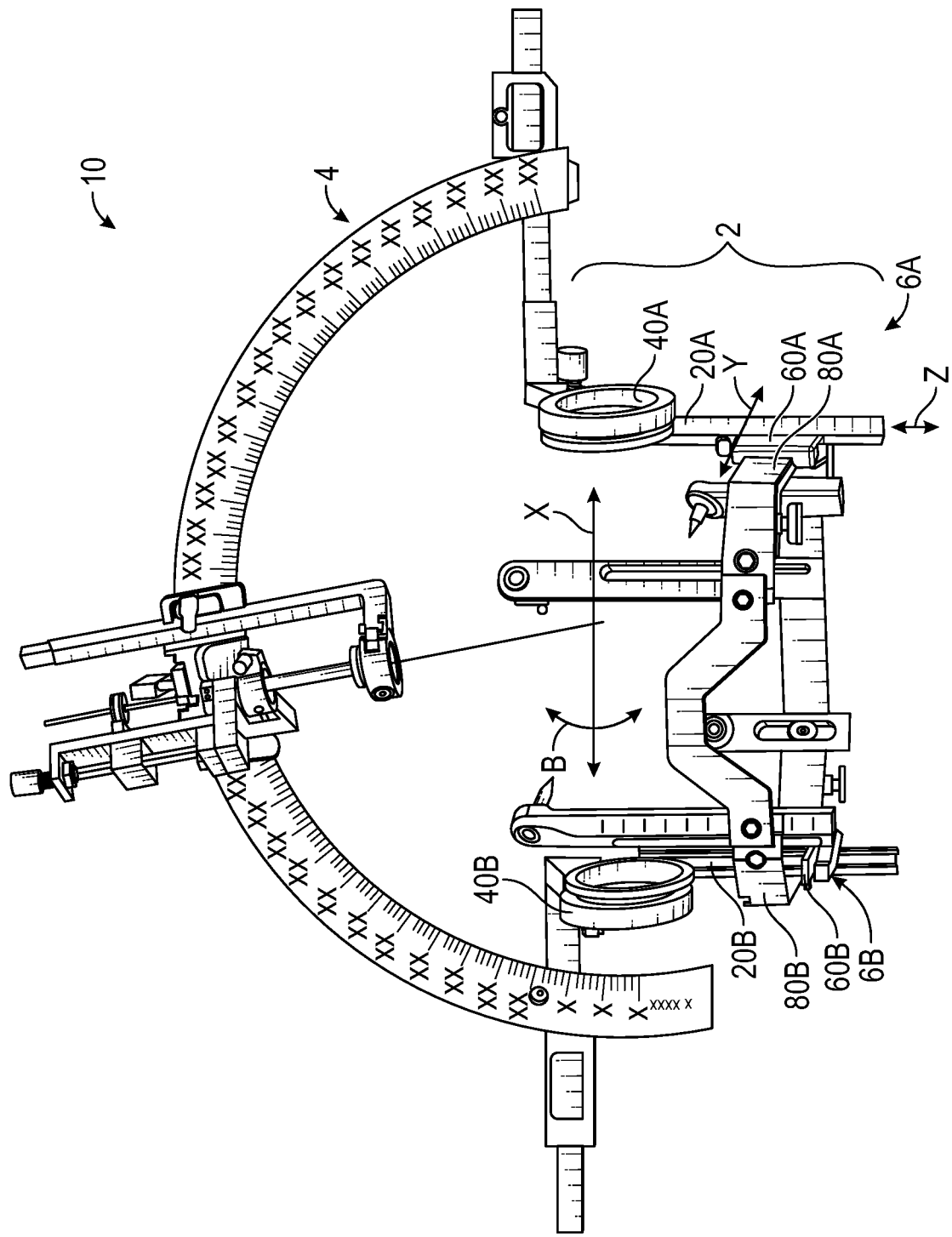
FIG. 1A is a front perspective view showing a Leksell frame for use in stereotaxy-guided surgery.

Various embodiments of a stereotactic coordinate adjuster for use with a stereotactic frame are disclosed herein. In particular, the stereotactic coordinate adjuster is configured for adjusting position and providing additional stability to an adjustment mechanism of a stereotactic frame. The stereotactic coordinate adjuster includes a locator that enables fine adjustment of a position of a Y-rack and a Z-rack that each engage with components of a stereotactic frame for stable adjustment of the stereotactic frame along a Y-direction and a Z-direction. The stereotactic coordinate adjuster further includes a ring support mechanism for supporting an arc portion of the stereotactic frame, thereby allowing further support of the stereotactic frame about its pivoting horizontal axis. Referring to the drawings, embodiments of a system for stereotactic coordinate adjustment are illustrated and generally indicated as 100 in FIGS. 2-10E.

Stereotactic Frame System

Figure 1B:
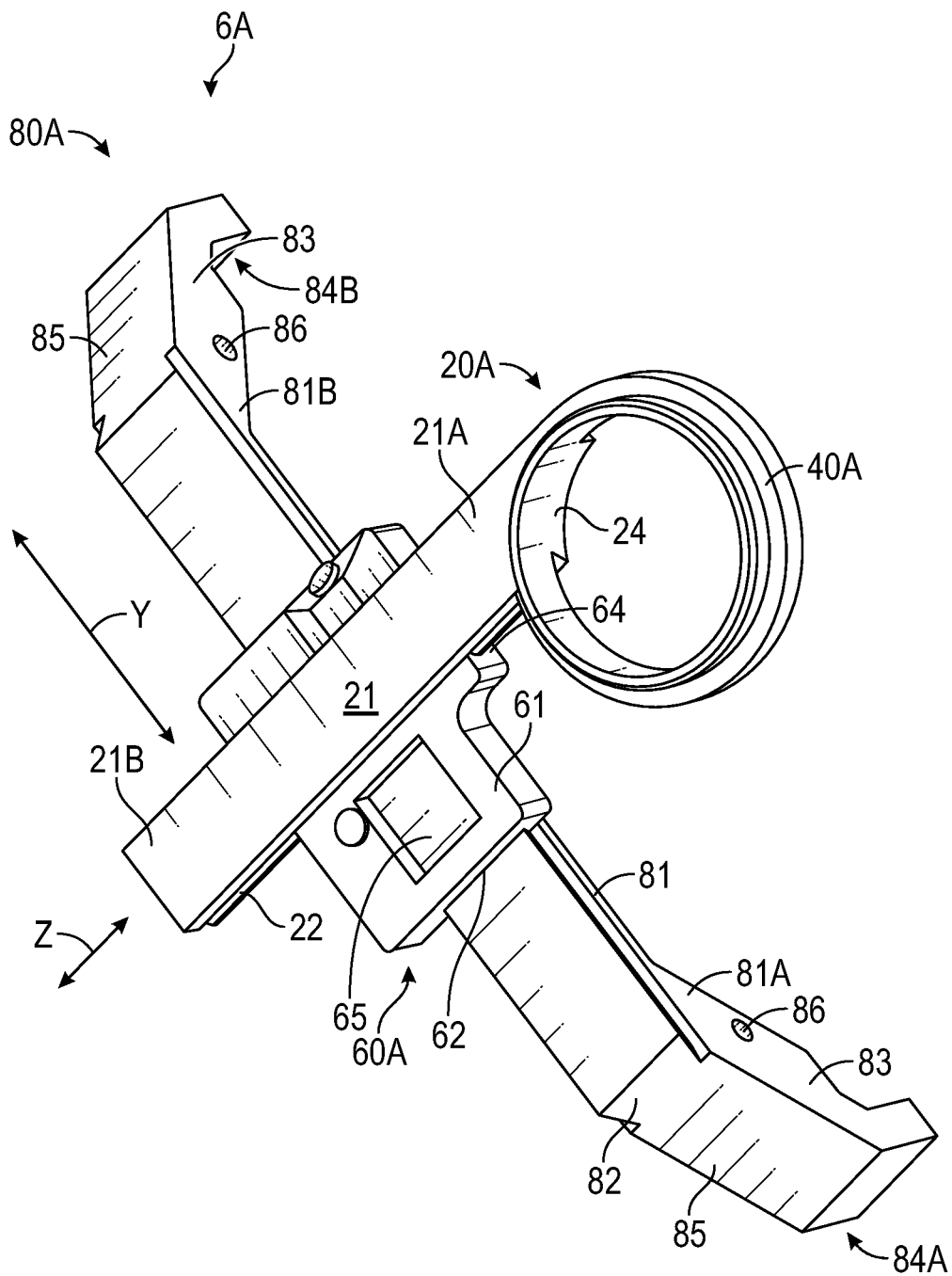
FIG. 1B is a side perspective view showing a slide portion and a frame portion of the Leksell frame of FIG. 1A.
Figure 2:
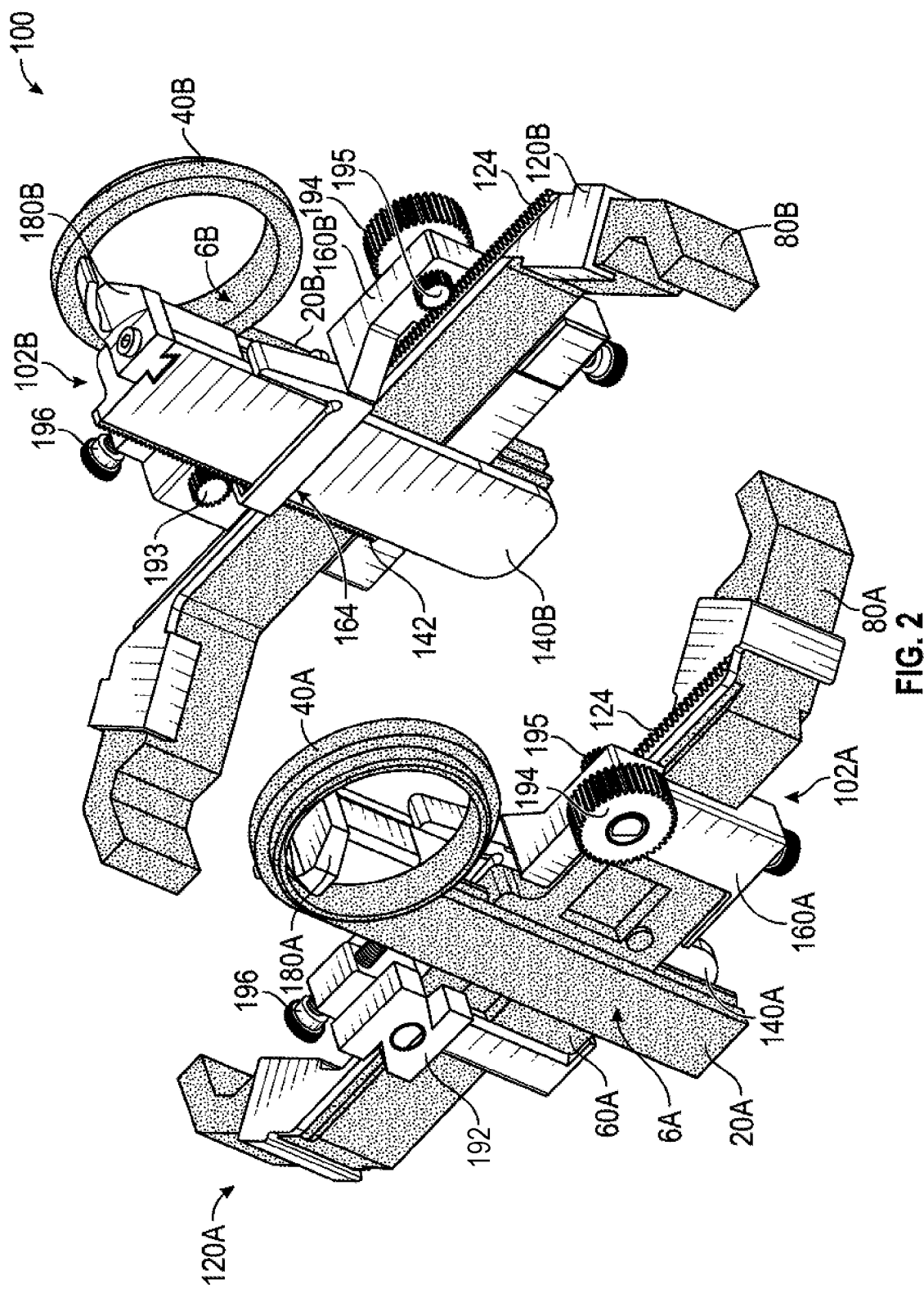
FIG. 2 is a first side perspective view showing a stereotactic coordinate adjuster for the Leksell frame of FIG. 1A.

A Stereotactic frame system 10 is illustrated in FIGS. 1A and 1B to provide context for the stereotactic coordinate adjuster system 100 of FIGS. 2-10E. In some embodiments, stereotactic frame system 10 is a Leksell system. The stereotactic frame system 10 includes a crown portion 2 coupled to an arc portion 4, the crown portion 2 including a left portion 6A and a right portion 6B in which the left and right portions 6A and 6B each respectively define a first frame portion 80A and an opposite second frame portion 80B collectively configured for receipt of a human head. As shown in FIG. 1A, first frame portion 80A and second frame portion 80B are each positioned at opposite sides of the stereotactic frame system 10 and are both oriented along horizontal axis Y. As further shown, a first arc support member 20A is associated with the first frame portion 80A by a left slide portion 60A and an opposite second arc support member 20B is associated with second frame portion 80B by a right slide portion 60B. In some embodiments, the arc support member 20A defines a first ring 40A and the second arc support member 20B defines a second ring 40B. FIG. 1B illustrates the left portion 6A isolated from the right portion 6B, however it should be noted that respective components of the left portion 6A are identical to their counterpart of the right portion 6B. Problems that typically arise from use of a conventional stereotactic frame system 10 include cumbersome and/or imprecise fine manual adjustment of the arc support members 20A and 20B in the Y and Z directions relative to the respective frame portions 80A and 80B.

Figure 3:
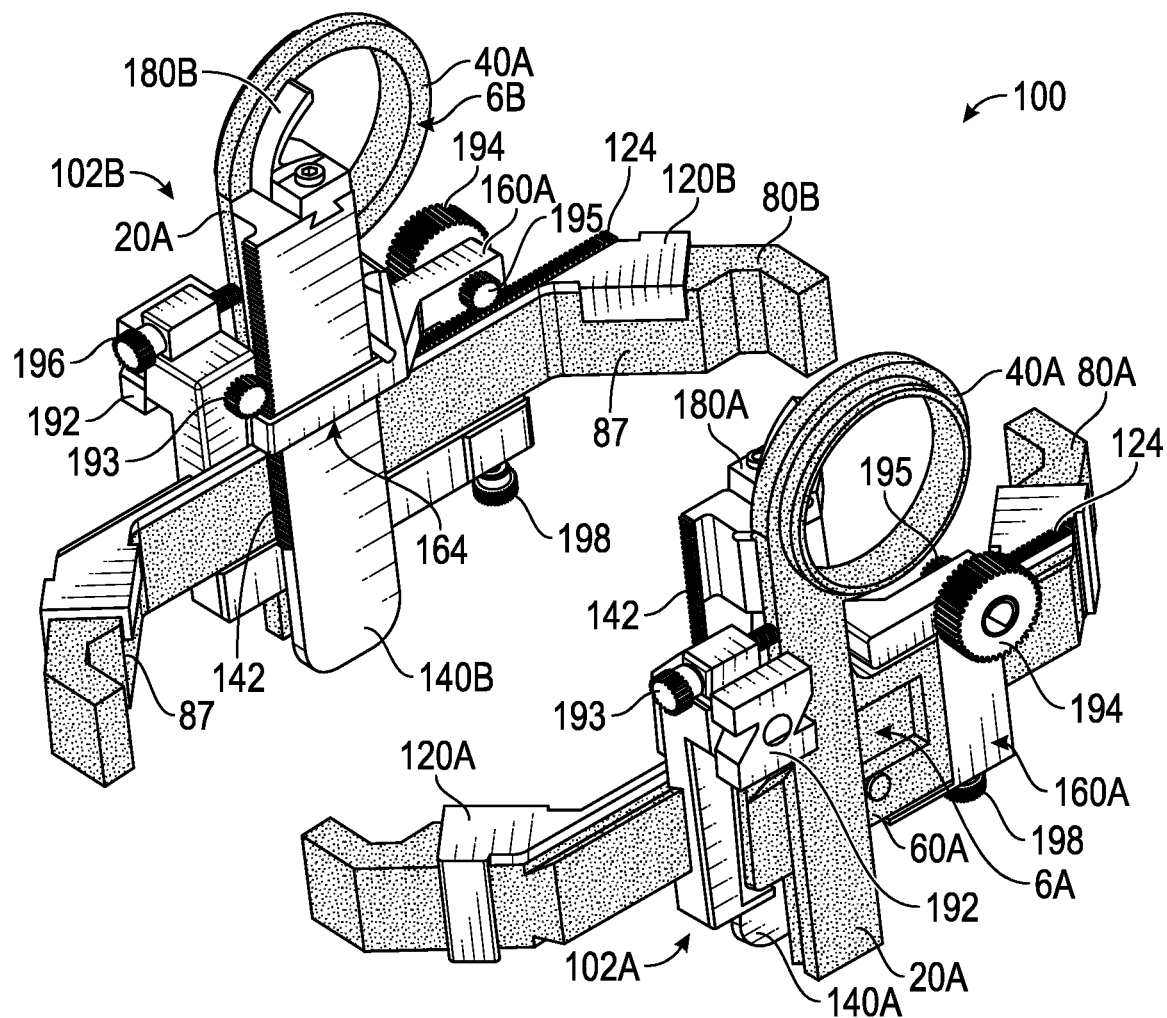
FIG. 3 is a second side perspective view showing the stereotactic coordinate adjuster of FIG. 2.
Figure 4:
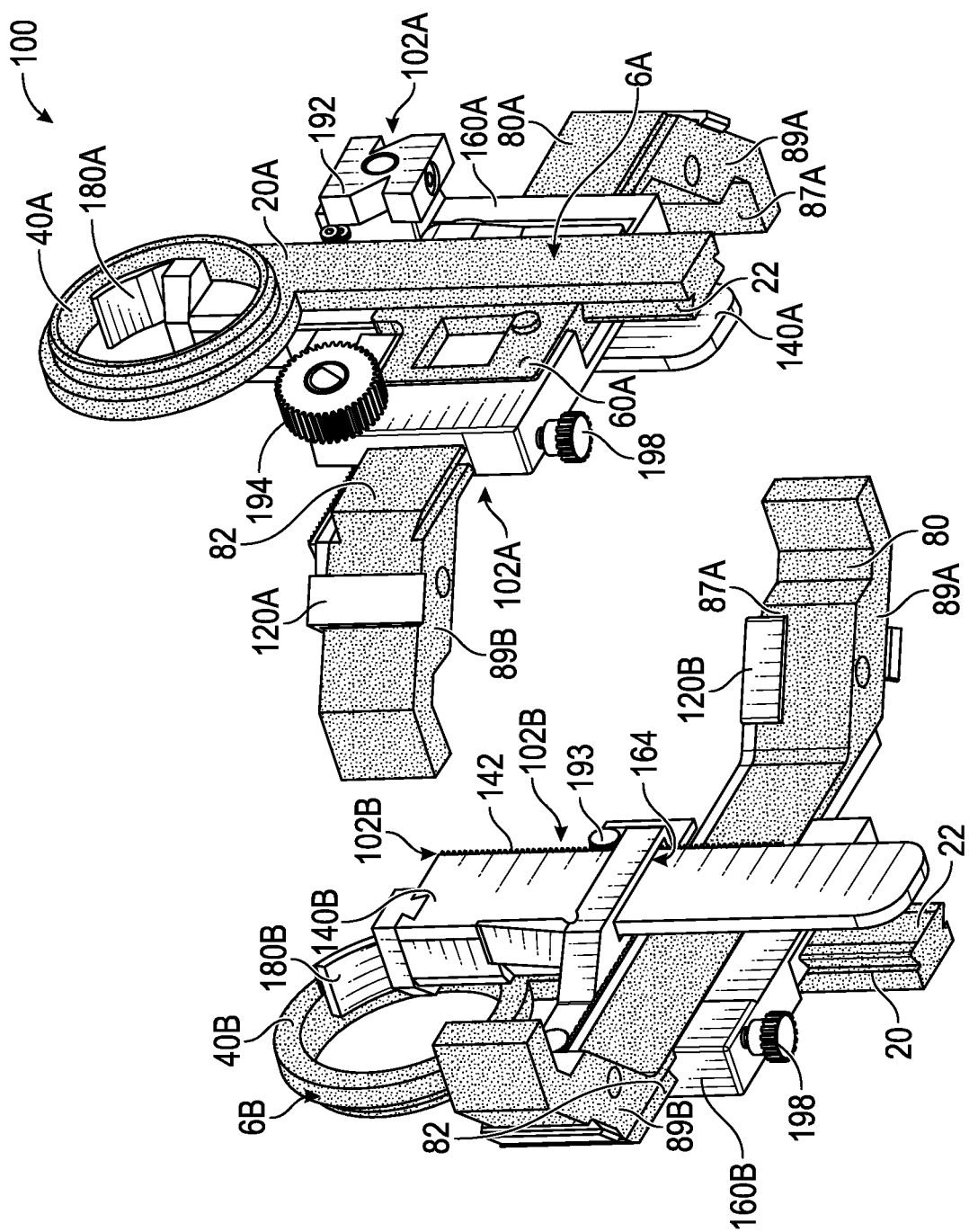
FIG. 4 is a third below perspective view showing the stereotactic coordinate adjuster of FIG. 2.

For simplicity and brevity, sub-components of the frame portions 80A and 80B will be discussed in terms of left frame portion 80A only; however, it should be noted that the description of the left frame portion 80A and its sub-components equally applies to the description of the right frame portion 80B and its identical sub-components. Referring to FIG. 1B, the frame portion 80A of left portion 6A includes a frame rail 81 having a first shoulder 84A defined at a first end 81A of the frame rail 81 and a second shoulder 84B defined at a second end 81B of the frame rail 81. Frame portion 80A includes shoulders 84A and 84B defined at respective ends 81A and 81B of the frame portion 80A. Shoulders 84A and 84B each define a topside 83, an outer side 85, an inner side 87 (FIGS. 3 and 4), and an underside 89 (FIG. 4). In some embodiments, the topside 83 for each respective shoulder 84A and 84B includes an alignment hole 86, typically used to align MR indicator plates used for imposing fiducials during imaging. Further, frame rail 81 includes a dovetail portion 82 along an outer side of the frame rail 81 for engagement with the Y-receptacle 62 of the slide portion 60A.

As shown, the arc support members 20A and 20B are each oriented along vertical direction Z in perpendicular relation to their associated frame rail 81, wherein each frame rail 81 is oriented along horizontal axis Y and provides structural support for the arc portion 4. Arc support member 20A defines an elongated body 21 including a top portion 21A defining a ring 40A and a bottom portion 21B defining a dovetail portion 22. Similarly, arc support member 20B also defines identical components and features. The rings 40A and 40B are collectively configured to receive the arc portion 4 for effecting rotation of the arc portion 4 in either a clockwise or counterclockwise rotational direction B (FIG. 1A) about horizontal axis X.

For simplicity, description of the sub-components of the arc support members 20A and 20B will be discussed in terms of left arc support member 20A with respect to left slide portion 60A, however it should be noted that the same applies to right arc support member 20B with respect to right slide portion 60B. Referring directly to FIG. 1B, arc support member 20A is associated with ring 40A by a shoulder 24 which partially forms a section of the ring 40A. The elongated body 21 extends below the shoulder 24 and includes the dovetail portion 22 defined along the bottom portion 21B of the arc support member 20A. The dovetail portion 22 engages the Z-receptacle 64 of the slide portion 60A such that the arc support member 20A can be lifted or lowered in the vertical direction Z relative to the slide portion 60A. Similarly, sub-components described herein also apply to arc support member 20B with respect to left slide portion 60B.

As further shown, each arc support member 20A and 20B is coupled to its respective frame portion 80A and 80B by a slide 60A and 60B. For simplicity, sub-components of the slide portions 60A and 60B will be discussed in terms of left slide portion 60A, however it should be noted that the same description applies to right slide portion 60B. In some embodiments, the slide 60A defines a slide body 61, a Y-receptacle 62 for receipt of the frame portion 80A and a Z-receptacle 64 for receipt of the arc support member 20A. The slide 60A allows the arc support member 20A to be positioned along the frame portion 80A by moving the slide 60A, and consequently the arc support member 20A, in either a left or right direction along the Y axis defined by the frame portion 80A. In some embodiments, the slide 60A further includes a window 65 for viewing one or more markings along the frame portion 80A that denote horizontal position of the slide 60A relative to the frame portion 80A. The slide 60A further allows the arc support member 20A to be raised or lowered in the vertical direction Z relative to the horizontal axis Y. Similarly, sub-components described herein also apply to slide 60B with respect to frame portion 80B and arc support member 20B.

Stereotactic Coordinate Adjuster

Referring to FIGS. 2-5, the stereotactic coordinate adjuster system 100 provides fine adjustability to the stereotactic frame system 10. Stereotactic coordinate adjuster system 100 includes a left coordinate adjuster 102A and a right coordinate adjuster 102B, each corresponding with a respective left portion 6A and right portion 6B of the stereotactic frame system 10. The left and right coordinate adjusters 102A and 102B each include respective locators 160A and 160B configured to encapsulate respective slides 60A and 60B. Coordinate adjusters 102A and 102B further include respective Y-racks 120A and 120B in association with the respective locators 160A and 160B, each configured to engage with respective frame portions 80A and 80B of the stereotactic frame system 10. In addition, the coordinate adjusters 102A and 102B further include respective Z-racks 140A and 140B in association with the respective locators 160A and 160B, each configured to engage respective arc support members 20A and 20B of the stereotactic frame system 10. The operative association between the locators 160A and 160B and Y-racks 120A and 120B provide fine adjustment of a horizontal (along axis Y) position of the locators 160A and 160B as well as providing a concurrent fine adjustment of the arc support members 20A and 20B along the frame portions 80A and 80B of the stereotactic frame system 10. Similarly, the operative association between the locators 160A and 160B and Z-racks 140A and 140B also provide fine adjustment of the vertical position (along axis Z) of the Z-racks 140A and 140B as well as providing the concurrent fine adjustment of the arc support members 20A and 20B of the stereotactic frame system 10.

Rings 40A and 40B are each supported by respective ring support assemblies 180A and 180B in which each ring support assembly 180A and 180B is associated with a respective Z-rack 140A and 140B for maintaining contact with the rings 40A and 40B of the arc support members 20A and 20B. In addition, each Z-rack 140A and 140B engages its respective locator 160A and 160B by insertion of a respective Z-rack 140A and 140B into its respective locator 160A and 160B.

For simplicity, sub-components of the Y-racks 120A and 120B, Z-racks 140A and 140B, and locators 120A and 120B will be discussed in terms of left Y-rack 120A, left Z-rack 140A, and left locator 160A only; however, it should be noted that the same applies to right Y-rack 120B, right Z-rack 140B and right locator 160B. Y-rack 120A includes a gear rack 124 and an associated Y-dial 194. Similarly, Z-rack 140A includes a gear rack 142 and associated Z-dial 192. The Y-dial 194 is associated with a respective Y-pinion 195 for engagement with the gear rack 124 of the Y-rack 120A for positional adjustment of the locator 160A and associated slide 60A along the horizontal axis Y. Similarly, the Z-dial 192 is associated with a respective Z-pinion 193 for engagement with the gear rack 142 of the Z-rack 140A for positional adjustment of the Z-rack 140A and associated arc support member 20A along the vertical axis Z. The locator 120A furthers includes a Y-bolt 198 for fixing positions of the locator 120A along the horizontal axis Y and a Z-bolt 196 for fixing the position of the Z-rack 140A along the vertical axis Z.

Locator

Referring to FIGS. 5-6C and 10C, the locators 160A and 160B of the stereotactic coordinate adjuster system 100 are each configured to receive respective slide portions 60A and 60B of the stereotactic frame system 10. The locators 160A and 160B each provide a means for moving respective slide portions 60A and 60B in the Y-direction means for moving the arc support members 20A and 20B in the Z-direction, and a means for more securely mounting the arc support members 20A and 20B on the frame portions 80A and 80B of the stereotactic frame system 10.

For simplicity, sub-components of the locators 120A and 120B will be discussed in terms of left locator 160A with respect to left Z-rack 140A, left Y-rack 120A, left slide portion 60A, left frame portion 80A and left arc support member 20A; however, it should be noted that the same description applies to right locator 160B with respect to right Z-rack 140B, right Y-rack 120B, right slide portion 60B, right frame portion 80B and right arc support member 20B. In some embodiments, the locator 160A defines a generally rectangular body 161 including a slide receptacle 162 defined through the body 161. In some embodiments, the body 161 defines a front portion 161A and an opposing rear portion 161B, in which the front portion 161A includes a slide receptacle 162 as well as engagement points for Z-dial 192 and Y-dial 194. As shown, the opposing rear portion 161B defines a track 171. In some embodiments, when engaged with slide portion 60A, the track 171 aligns with the Y-receptacle 62 of the slide portion 60A for receipt of the frame portion 80A of the stereotactic frame system 10.

Figure 5:
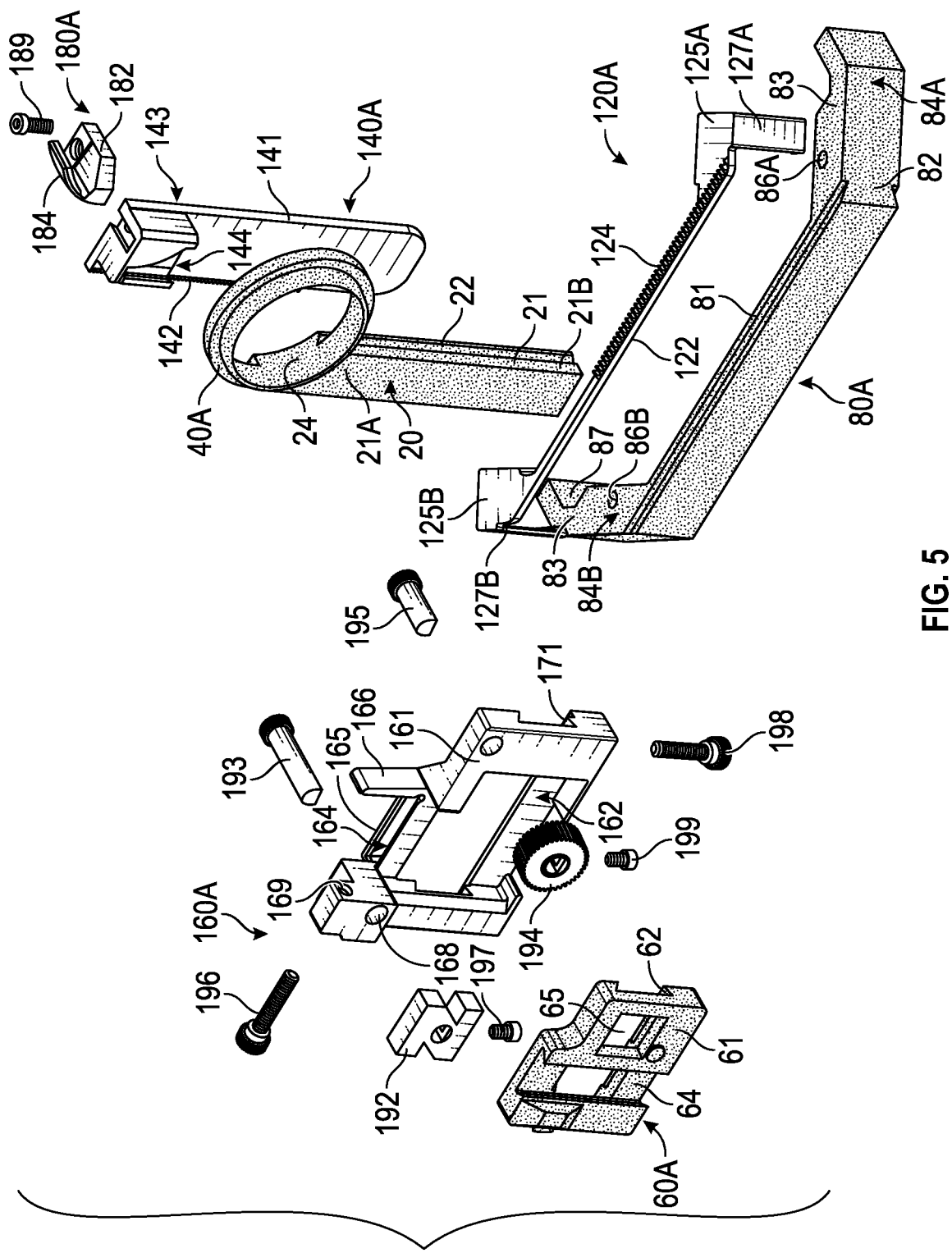
FIG. 5 is an exploded view showing the stereotactic coordinate adjuster of FIG. 2.
Figure 6A:
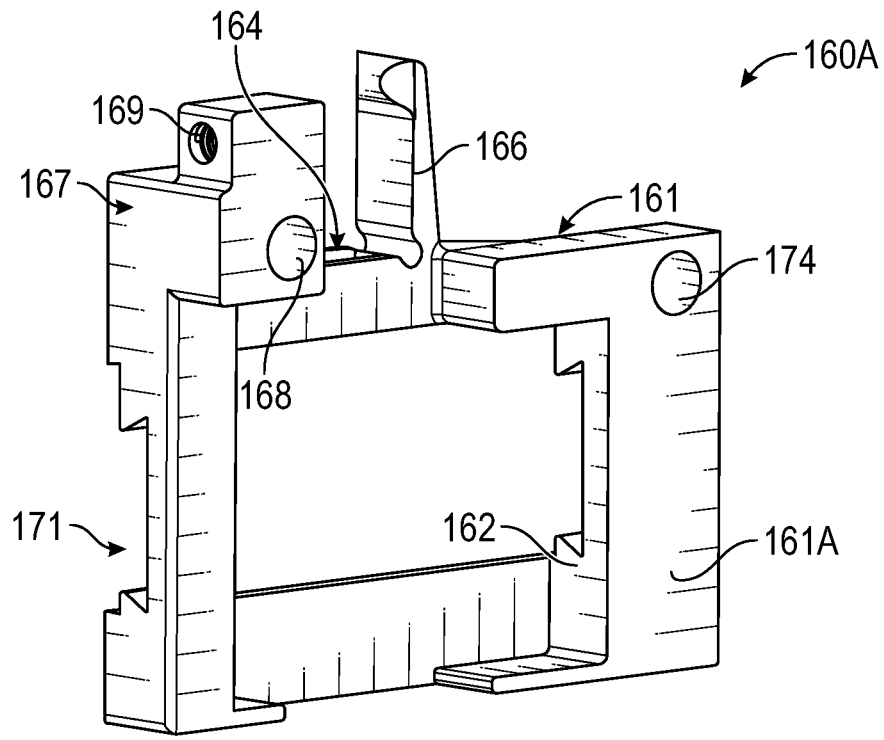
FIG. 6A is a front perspective view showing a locator of the stereotactic coordinate adjuster of FIG. 2.
Figure 6B:
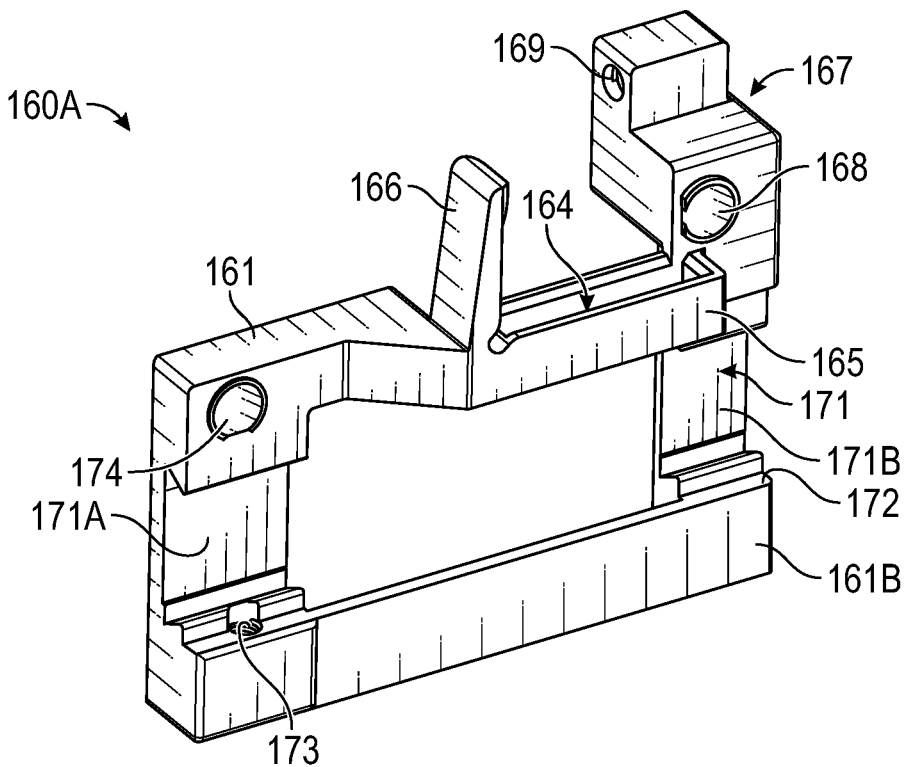
FIG. 6B is a rear perspective view showing the locator of FIG. 6A.
Figure 6C:
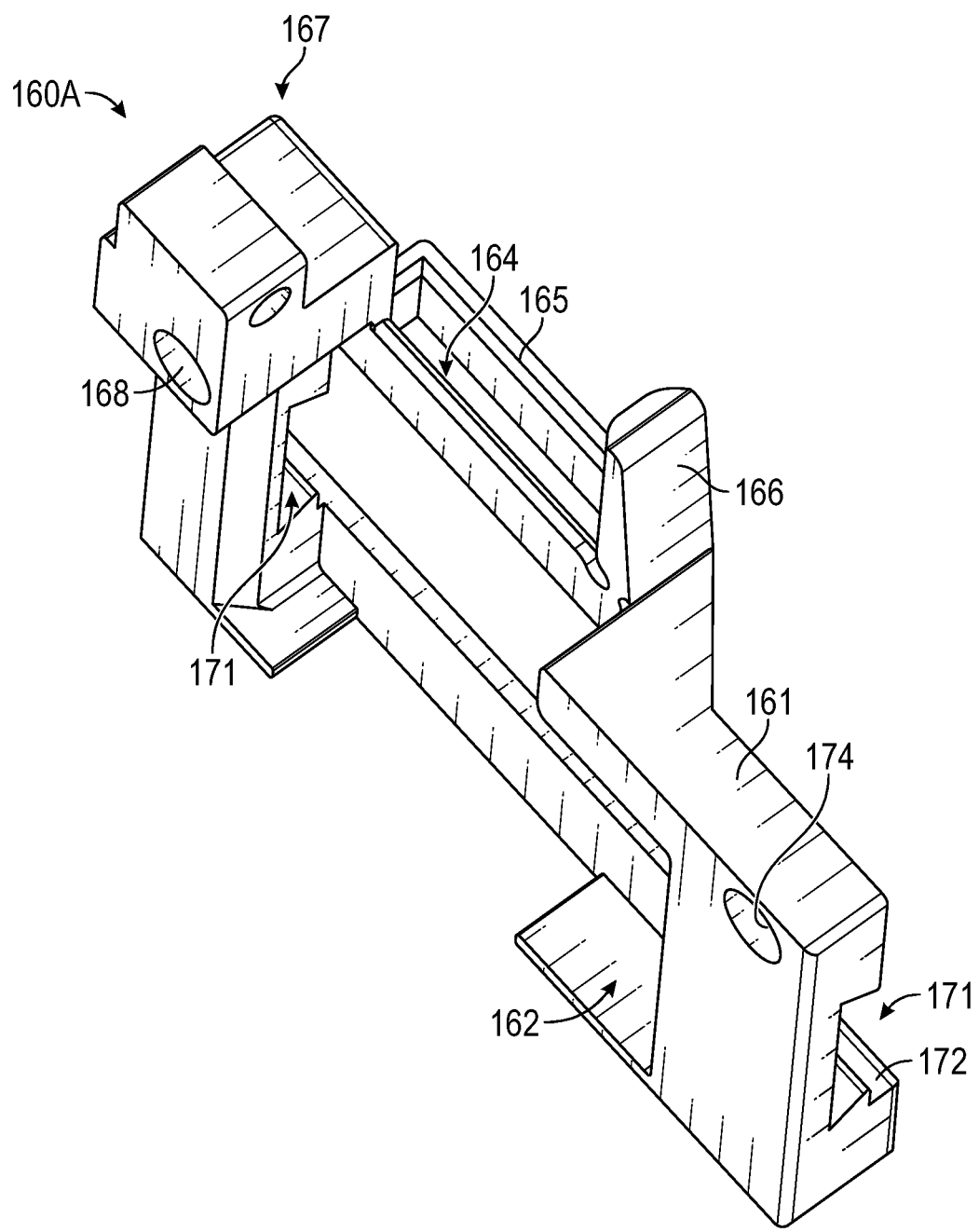
FIG. 6C is a top perspective view showing the locator of FIG. 6A.

In another aspect, as specifically shown in FIG. 6C, the rear portion 161B of the locator 160A includes a Z-rack guide slot 164 configured to receive the Z-rack 140A when the arc support member 20A and Z-rack 140A are engaged with the locator 160A. The Z-rack guide slot 164 is collectively formed by the rear portion 161B and a guide portion 165 that extends from the rear portion 161B of the body 161. Z-rack guide slot 164 is further associated with a tensioner element 166 configured to stabilize the Z-rack 140A (FIG. 5) with respect to the locator 160A. In particular, during operation, tensioner element 166 applies a bias to the Z-rack 140A, thereby reinforcing the alignment of the Z-rack 140A and associated arc support member 20A within the locator 160A that pushes the gear rack 142 towards the Z-pinion 193 (FIG. 5) for improved traction.

In another aspect, as specifically shown in FIGS. 5 and 6B, the rear portion 161B of the locator 160A includes the track 171 for receipt of the dovetail portion 82 of frame portion 80A of the stereotactic frame system 10. In some embodiments, the track 171 includes a first track portion 171A set apart from a second track portion 171B with the slide receptacle 162 defined between the first and second track portions 171A and 171B. During assembly, engagement of the slide 60 with the slide receptacle 162 collectively forms the entirety of the track 171. The track 171 forms a notch configured for secure receipt of the dovetail portion 82 of the frame portion 80A. The track 171 can be fully or partially supported by the track base 172, which also forms a lower portion of the slide receptacle 162.

The locator 160A of the stereotactic coordinate adjuster system 100 further serves as a mounting mechanism for an assembly of dials, screws and pinions that serve to adjust and lock the positions of the frame portion 80A and arc support member 20A relative to one another. In some embodiments, the locator 160A includes a Z hardware block 167 configured to provide engagement points and support for a Z-bolt 196, Z-dial 192 and associated Z-pinion 193 for engagement of the gear rack 142 of the Z-rack 140. The locator 160A further includes engagement points and support for a Y-bolt 198, Y-dial 194 and associated Y-pinion 195 for engagement of a gear rack 124 of the Y-rack 120A.

In particular, Z hardware block 167 includes a Z-pinion channel 168 defined along the horizontal direction X, and a Z-bolt channel 169 defined along the horizontal direction Y. Z-dial 192 engages or is integral with Z-pinion 193 in which the direction of elongation of the Z-pinion 193 aligns with horizontal axis X (FIG. 5) for insertion through a Z-pinion channel 168 of the Z hardware block 167. Z-pinion 193 engages with the gear rack 142 of the Z-rack 140A such that as the Z-dial 192 is rotated in a first rotational direction or an opposite second rotational direction. Similarly, the Z-pinion 193 is engaged with the gear rack 142 and is similarly rotated such that the Z-rack 140A and associated arc support member 20A of the stereotactic frame system 10 may be lifted or lowered relative to the locator 160A. In assembly, the Z-bolt 196 is inserted through the Z-bolt channel 169 such that a distal end 196A of the Z-bolt 196 contacts the arc support member 20A to slow or halt the movement of the arc support member 20A for fine adjustment or preventing unwanted movement during tightening of components of the stereotactic frame system 10. Further, in some embodiments, a screw 197 is used to couple the Z-pinion 193 and Z-dial 192.

Similarly, locator 160A further includes a Y-pinion channel 174 defined along the horizontal direction X and located opposite to the Z hardware block 167 for receipt of the Y-pinion 195. The locator 160A also includes a Y-bolt channel 173 located within the track 171 of the locator 160A for receipt of the Y-bolt 198 such that the Y-bolt channel 173 is defined along the vertical direction Z. The Y-dial 194 engages or is otherwise integral with Y-pinion 195. The direction of elongation of the Y-pinion 195 aligns with horizontal axis X (FIG. 5) for insertion through the Y-pinion channel 174. Y-pinion 195 engages with a gear rack 124 of the Y-rack 120A such that as the Y-dial 194 is rotated in a first rotational direction or an opposite second rotational direction in which the Y-pinion 195 is engaged with the gear rack 124 and is similarly rotated such that the locator 160A is moved to the left or the right along the respective Y-rack 120A and associated frame portion 80A of the stereotactic frame system 10. In addition, the Y-bolt 198 is inserted through the Y-bolt channel 173 such that a distal end 198A of the Y-bolt 198 contacts the associated frame portion 80A to slow or halt the movement of the locator 60A relative to the frame portion 80A for fine adjustment or preventing unwanted movement during tightening of components of the stereotactic frame system 10. Further, in some embodiments, a screw 199 couples the Y-pinion 195 and Y-dial 194. Sub-components described herein similarly apply to right locator 160B with respect to right Z-rack 140B, right Y-rack 120B, right slide portion 60B, right frame portion 80B and right arc support member 20B Z-Racks and Ring Supports Referring to FIGS. 5 and 7A-8D, the Z-racks 140A and 140B and associated ring support assemblies 180A and 180B are each configured to receive and support respective arc support members 20A and 20B and associated rings 40A and 40B of the stereotactic frame system 10. For simplicity, sub-components of the Z-racks 140A and 140B and associated ring support assemblies 180A and 180B will be discussed in terms of left Z-rack 140A and left ring support assembly 180A with respect to left locator 160A, left Y-rack 120A, left slide portion 60A, left frame portion 80A, left arc support member 20A and left ring portion 40A only; however, it should be noted that the same description applies to right Z-rack 140B and right ring support assembly 180B with respect to right locator 140B, right Y-rack 120B, right slide portion 60B, right frame portion 80B, right arc support member 20B, and right ring 40.

Figure 7A:
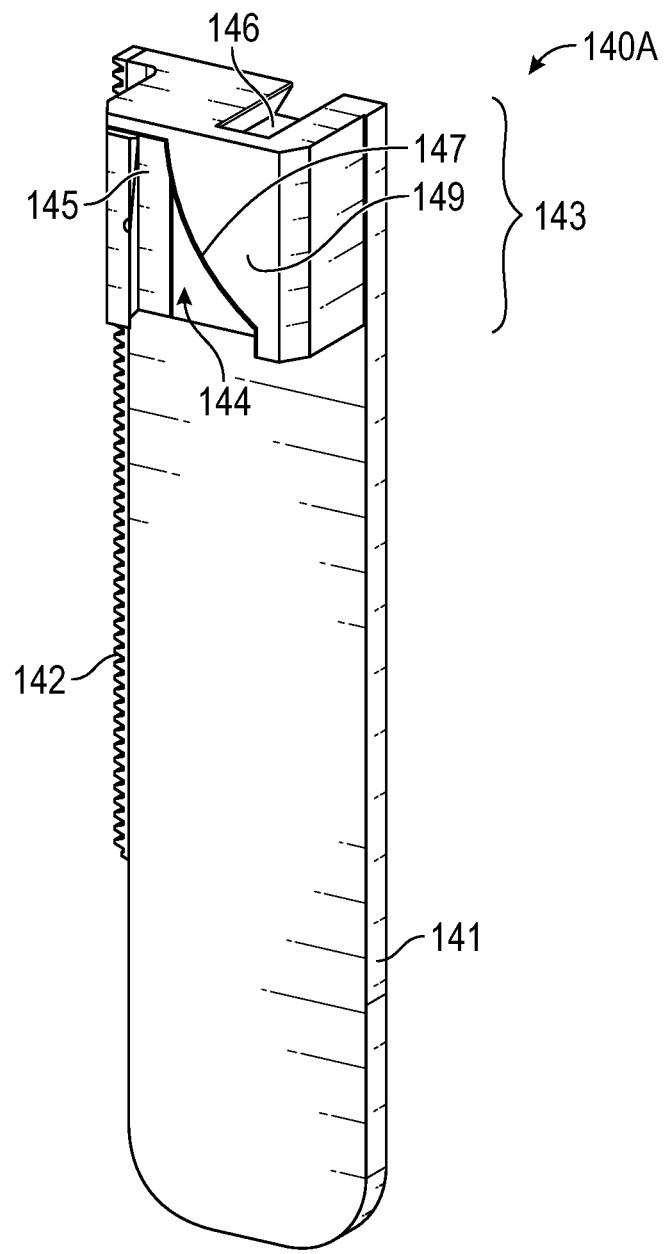
FIG. 7A is a front perspective view showing a spring-loaded "Z-rack" that allows stereotactic adjustment in the Z direction of the stereotactic coordinate adjuster of FIG. 2.
Figure 7B:
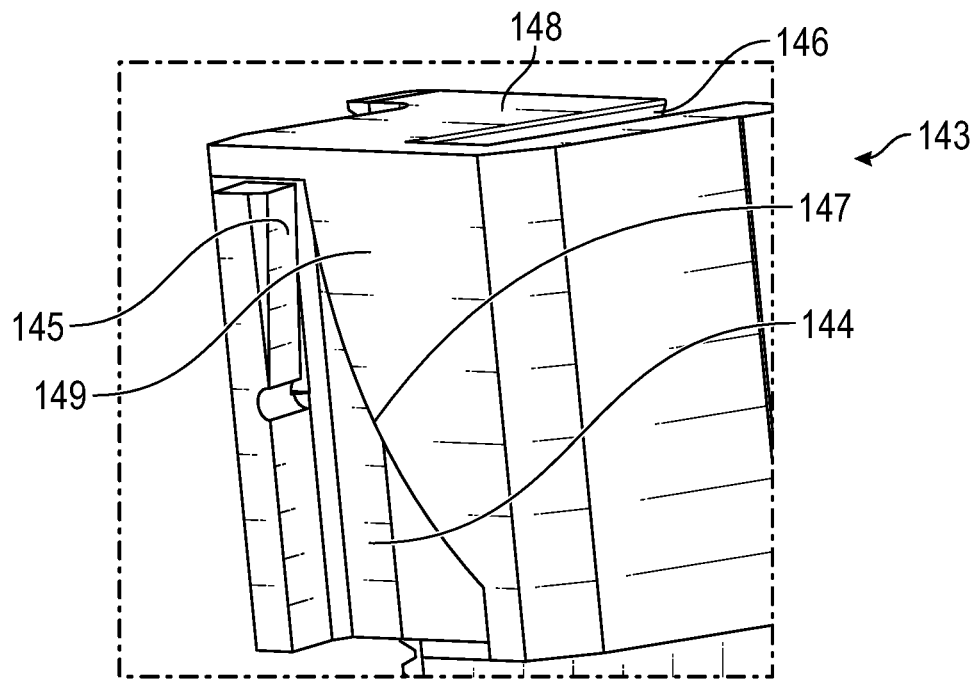
FIG. 7B is a magnified perspective view showing the spring-loaded Z-rack of FIG. 7A.
Figure 7C:
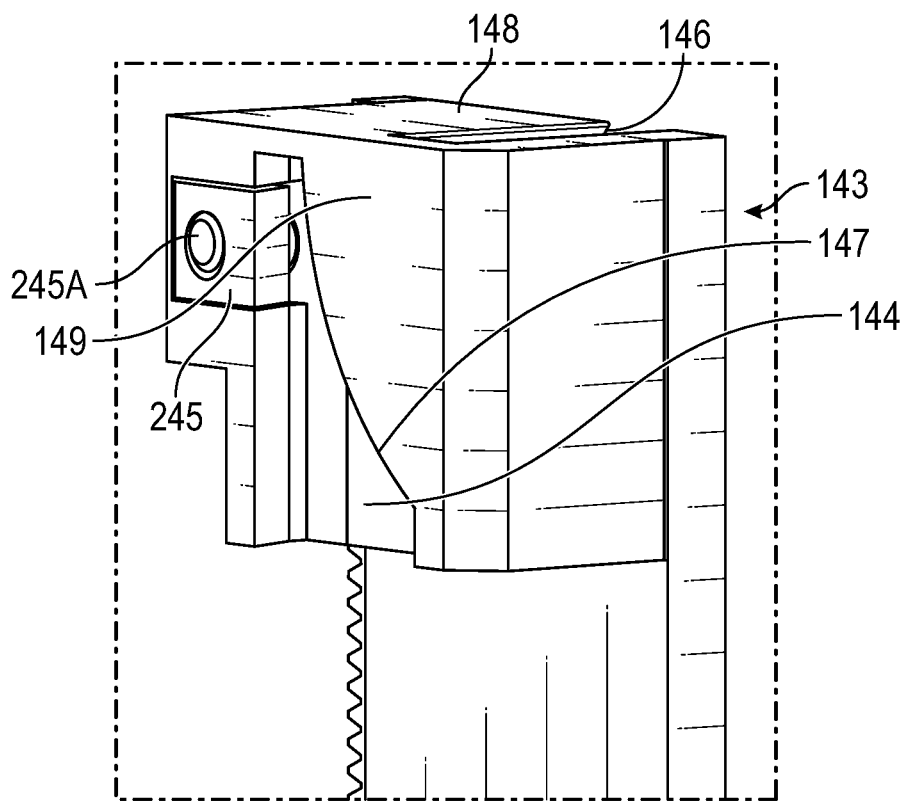
FIG. 7C is a front perspective view showing a screw-driven Z-rack that allows stereotactic adjustment in the Z direction of the stereotactic coordinate adjuster of FIG. 2.
Figure 7D:
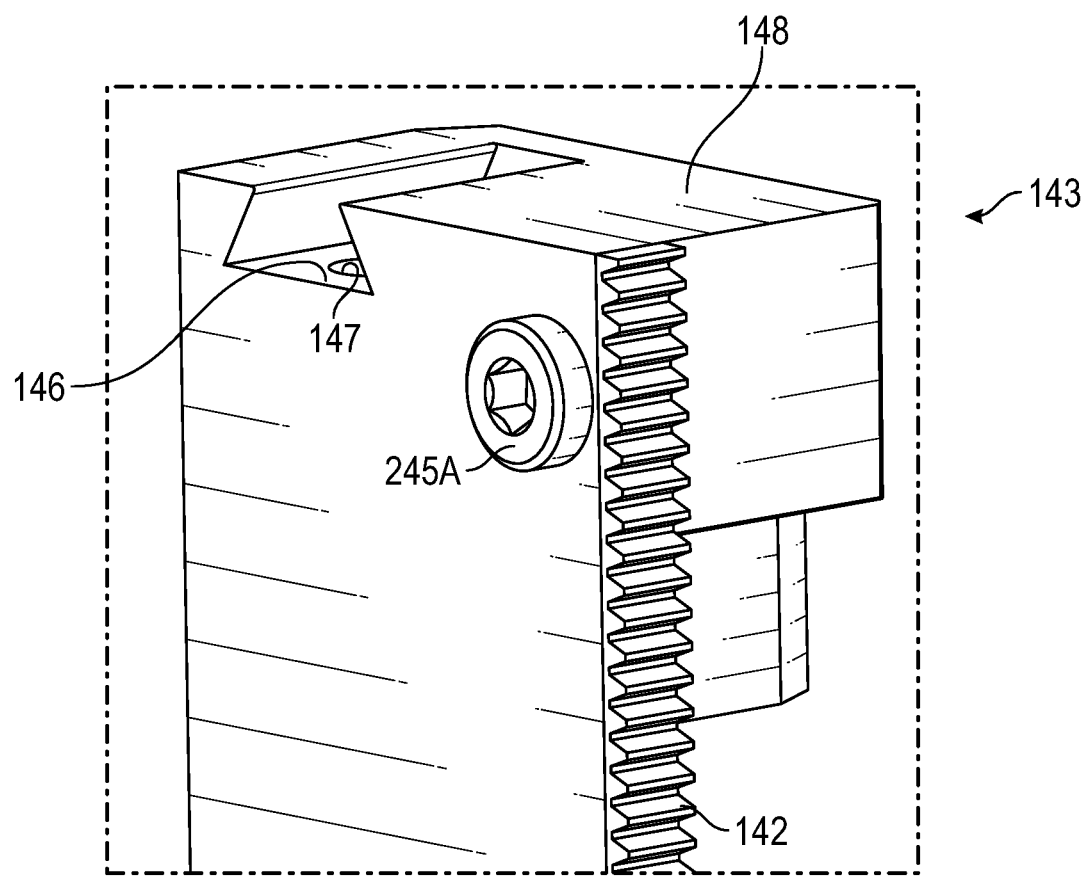
FIG. 7D is a rear perspective view showing the screw-driven Z-rack of FIG. 7C.
Figure 8B:
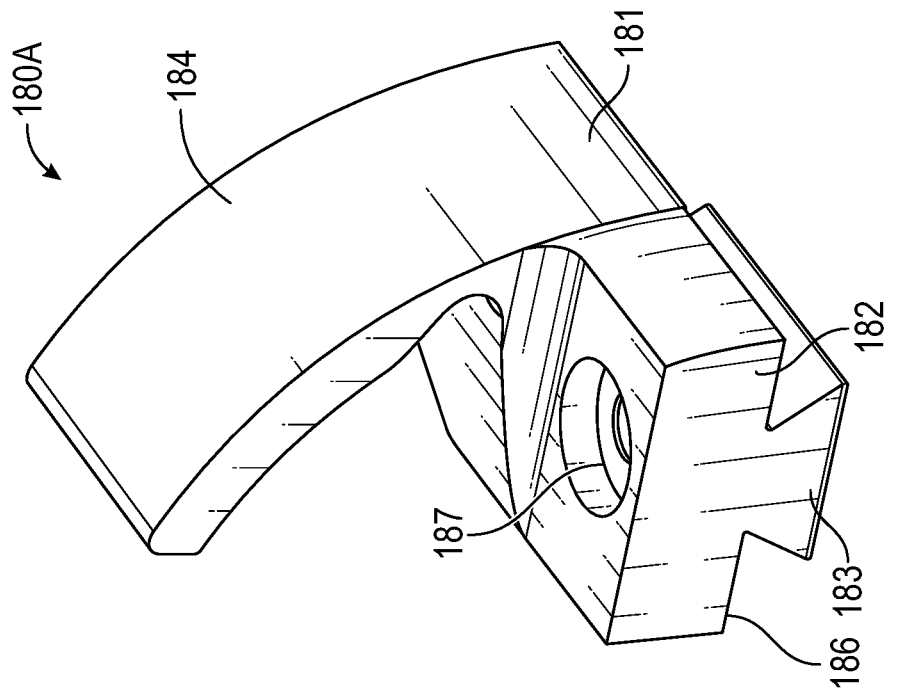
FIG. 8B is a rear perspective view showing the spring-loaded ring support of FIG. 8A.
Figure 8A:
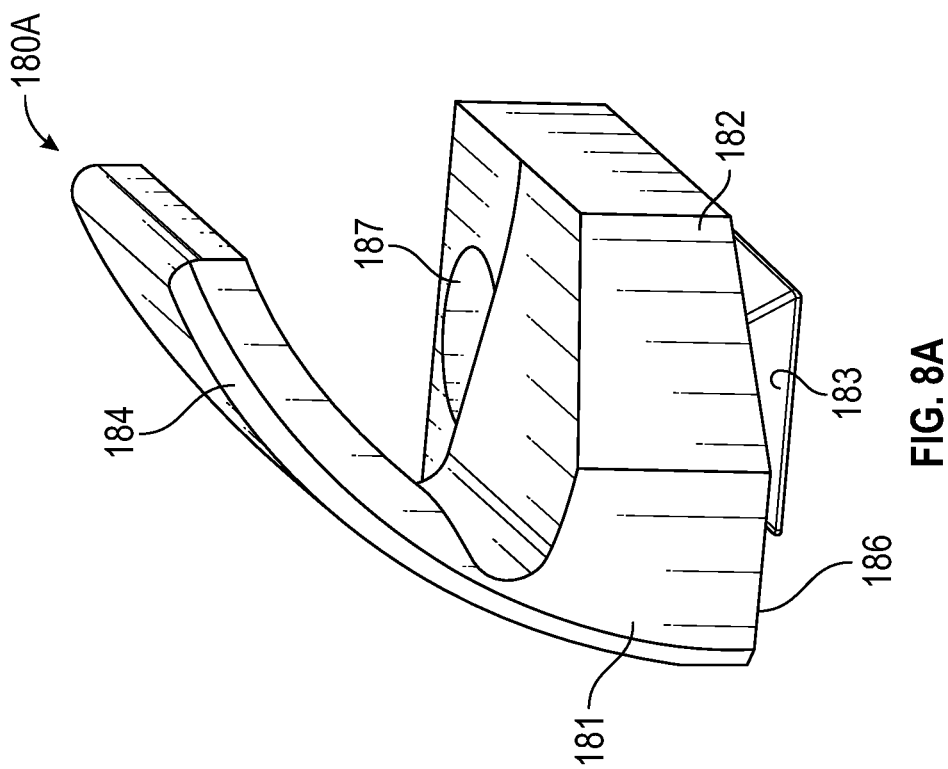
FIG. 8A is a front perspective view showing a spring-loaded ring support of the stereotactic coordinate adjuster of FIG. 2.
Figure 8D:
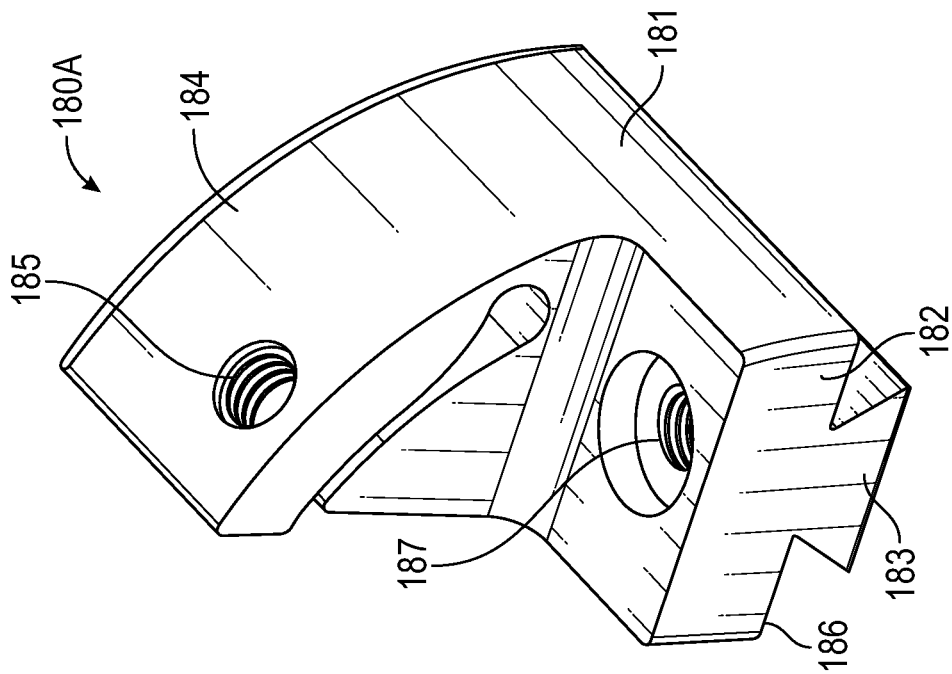
FIG. 8D is a rear perspective view showing the screw-driven ring support of FIG. 8C.
Figure 8C:
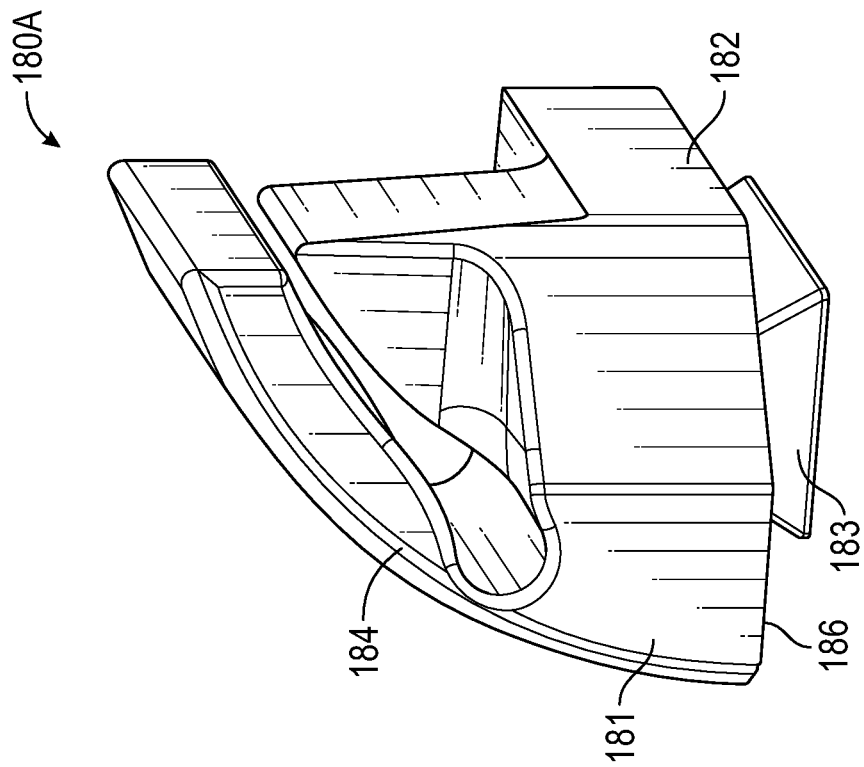
FIG. 8C is a front perspective view showing a screw-driven ring support of the stereotactic coordinate adjuster of FIG. 2.
Figure 9A:
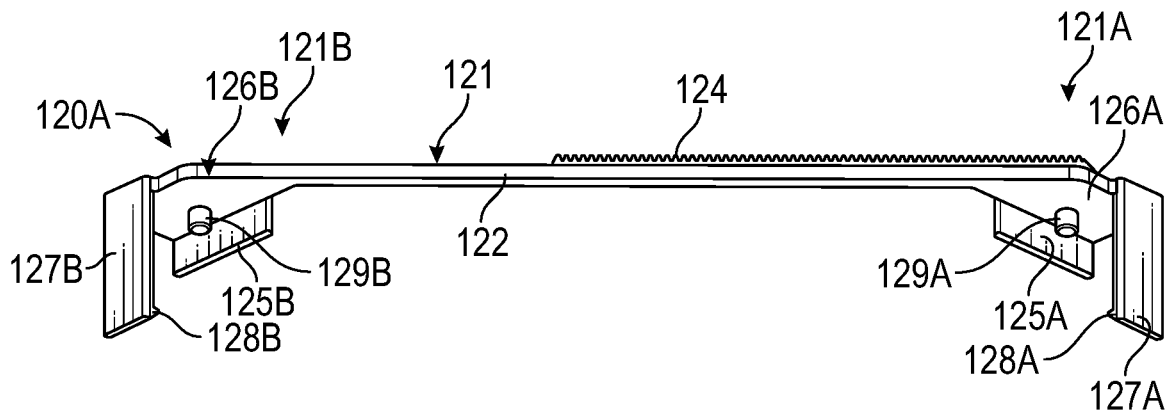
FIG. 9A is a perspective view showing a "Y-rack" that allows stereotactic adjustment in the Y direction of the stereotactic coordinate adjuster of FIG. 2.
Figure 9B:
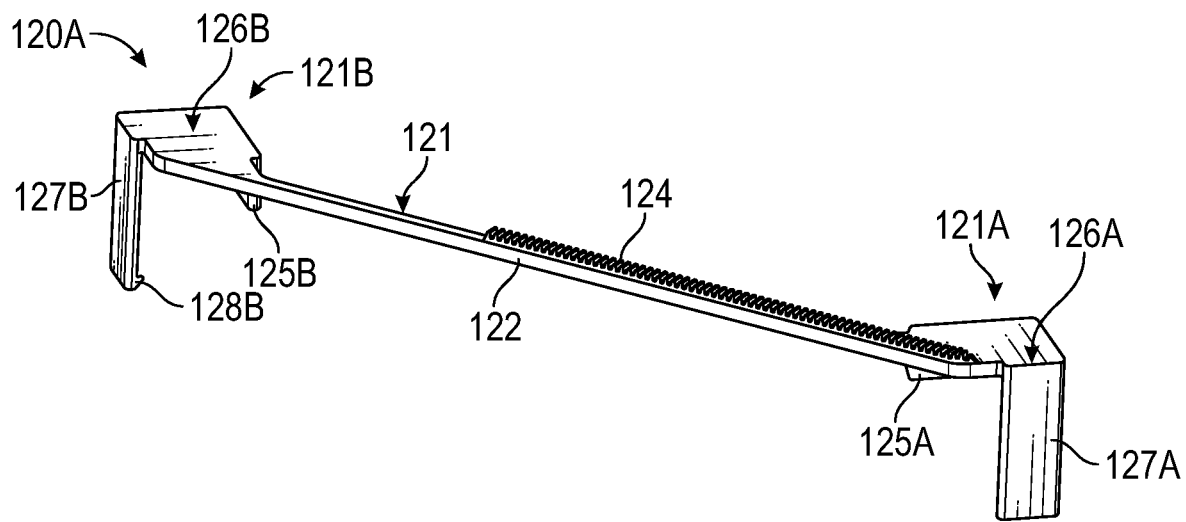
FIG. 9B is a top perspective view showing the Y-rack of FIG. 9A.

The Z-rack 140A includes an elongated body 141 defining a gear rack 142 along its side and a head portion 143, wherein the head portion 143 is configured to engage the ring shoulder 24 of arc support member 20A. In addition, the head portion 143 includes an arc shoulder receptacle 144 along a face 149 of the head portion 143 in association with a rail gripper mechanism 145 for encapsulating the ring shoulder 24 of arc support member 20A. As shown in FIG. 5, the arc shoulder receptacle 144 includes a curved recess 147 as well as a rail gripper mechanism 145/245 for engagement with the ring shoulder 24. In particular, FIG. 7B illustrates a first embodiment of the rail gripper mechanism 145 having a spring-loaded lever to aid in securing the top portion 21A of the arc support member 20A to the arc shoulder receptacle 144. FIG. 7C illustrates a second embodiment of the rail gripper mechanism 245 that includes a moveable block and a screw 245A for tightening the moveable block against the arc support member 20A to aid in securing the top portion 21A of the arc support member 20A to the arc shoulder receptacle 144. Curved recess 147 of the arc shoulder receptacle 144 encapsulates a portion of ring 40A. Head portion 143 further includes a ring support receptacle 146 defined at an upper face 148 of the head portion 143 for engagement of ring support assembly 180A. As shown in FIG. 7D, in some embodiments, the ring support receptacle 146 defines a notch configured to receive a dovetail stabilizer 183 of the ring support assembly 180A for secure coupling of the ring support assembly 180A to the Z-rack 140A.

Referring to FIGS. 5, 7A, 10B and 10E, the elongated body 141 defines the gear rack 142 of the Z-rack 140A. After engagement of the Z-rack 140A with the arc support member 20A, elongated body 141 of Z-rack 140A is inserted into the corresponding Z-rack guide slot 164 and the arc support member 20A is then inserted into the Z-receptacle 64 of the slide portion 60A such that the elongated body 141 of the Z-rack 140A and the arc support member 20A of the stereotactic frame system 10 straddle respective sides 161A and 161B of the locator 160A. The gear rack 142 engages with the Z-pinion 193 such that the gear rack 142 may be lifted or lowered relative to the locator 160A and slide 60A as the Z-dial 192 is rotated in a clockwise or counterclockwise rotational direction as shown in FIG. 3.

As shown in FIGS. 5 and 7A-8D, ring support assembly 180A includes a body 181 defining a base 182 configured for engagement with the ring support receptacle 146 of the head portion 143. In addition, the body 181 may define an arcuate lever 184 for respective engagement with the ring 40A. In some embodiments, the base 182 includes a base screw receptacle 187 for receipt of a base screw 189 (FIG. 5) that extends into the screw receptacle 147 of the ring support receptacle 146. The arcuate lever 184 maintains the engagement within the ring 40A along the curvature of the curved recess 147 to support the ring 40A. In some embodiments, the arcuate lever 184 includes a tensioning element (not shown) to further provide a bias against the interior of the ring 40A. In another embodiment, shown in FIGS. 8C and 8D, the arcuate lever 84 includes a lever screw receptacle 185 for receipt of a lever screw (not shown) that tensions or otherwise biases the arcuate lever 184 against the interior of the ring 40A. The base 182 of the body 181 further includes the dovetail stabilizer 183 defined along the underside 186 of the base 182 for engagement with the ring support receptacle 146 of the Z-rack 140A.

Y-Racks

Referring to FIGS. 5, and 9A-10A, the Y-racks 120A and 120B are configured to engage the frame portions 80A and 80B of the stereotactic frame system 10 to provide a manner to move the slide portions 60A and 60B and arc support members 20A and 20B in the Y-direction. For simplicity, sub-components of the Y-racks 120A and 120B will be discussed in terms of left Y-rack 120A with respect to left Z-rack 140A, left locator 160A, left slide portion 60A, left frame portion 80A, and left arc support member 20A only; however, it should be noted that the same description applies to right Y-rack 120B with respect to right Z-rack 140B, right locator 160B, right slide portion 60B, right frame portion 80B, and right arc support member 20B.

In particular, the Y-rack 120A provides a gear rack 124 oriented along the frame rail 81 of the frame portion 80A that engages the Y-pinion 195 of the locator 160A such that as the Y-pinion 195 is rotated in either a clockwise or counterclockwise direction, the locator 160A is moved in either a left direction or right direction along the horizontal axis Y. In some embodiments, the Y-rack 120A defines a body 121 defining a first end 121A and a second end 121B in which each end 121A and 121B includes a respective shoulder capsule 126A and 126B configured for engagement with respective shoulders 84A and 84B of the frame portions 80A and 80B. The shoulder capsules 126A and 126B each include a respective outer surface clip 127A and 127B for respective engagement with outer surfaces 85A and 85B of the frame portion 80A, as illustrated specifically in FIG. 10A. Each outer surface clip 127A and 127B includes a respective tang 128A or 128B defined along a respective bottom of each surface clip 127A and 127B that engages with a respective underside 89A and 89B of the shoulders 84A and 84B. Shoulder capsules 126A and 126B each include a respective inner surface tab 125A or 125B for engagement with a respective inner surface 87A and 87B of the shoulders 84A and 84B.

As shown, the Y-rack 120A includes a Y-rail portion 122 configured to align with the frame rail 81 of the frame portion 80A such that the Y-rail portion 122 sits atop the frame rail 81. A portion of the Y-rail 122 defines the gear rack 124 for engagement with the Y-pinion 195. In some embodiments, the Y-rack 120A defines one or more pins 129 along an underside of the Y-rack 120A for engagement with one or more alignment holes 86 of the frame portion 80A. In another embodiment, the Y-rack 120A does not need to rely on engagement with the alignment holes 86; rather, the Y-rack 120A can be positioned to conform with the shape of the frame portion 80A by the shoulder capsules 121A and 121B.

Method of Installation and Use

FIGS. 10A-10E illustrate a method of installing a coordinate adjuster 102A of the stereotactic coordinate adjuster system 100 onto the left portion 6A of the stereotactic frame system 10. For simplicity, sub-components of the coordinate adjusters 102A and 102B and left and right portions 6A and 6B will be discussed in terms of left coordinate adjuster 102A and left portion 6A; however, it should be noted that the same description applies to right coordinate adjuster 102B and right portion 6B.

Referring to FIG. 10A, the Y-rack 120A of the left coordinate adjuster 120A for the stereotactic coordinate adjuster system 100 is engaged with the frame portion 80A of the left portion 6A of the stereotactic frame system 10. In particular, the pins 129A and 129B of the Y-rack 120A are aligned with one or more alignment holes 86A and 86B of the frame portion 80A, and the Y-rack 120A is engaged with the frame portion 80A such that the shoulder capsules 126A and 126B of the Y-rack 120 encapsulate the respective shoulders 84A and 84B of the frame portion 80A. In addition the outer surface clips 127A and 127B of the Y-rack 120A engage with respective outer surfaces 85A and 85B of the frame portion 80A such that the respective tangs 128A and 128B of the outer surface clips 127A and 127B engage with the respective undersides 89A and 89B (FIG. 4) of the shoulders 84A and 84B. As shown, the gear rack 124 of the Y-rack 120 must orient upward to connect with the Y-pinion 195 of the locator 160A (FIGS. 10C and 10D).

Figure 10B:
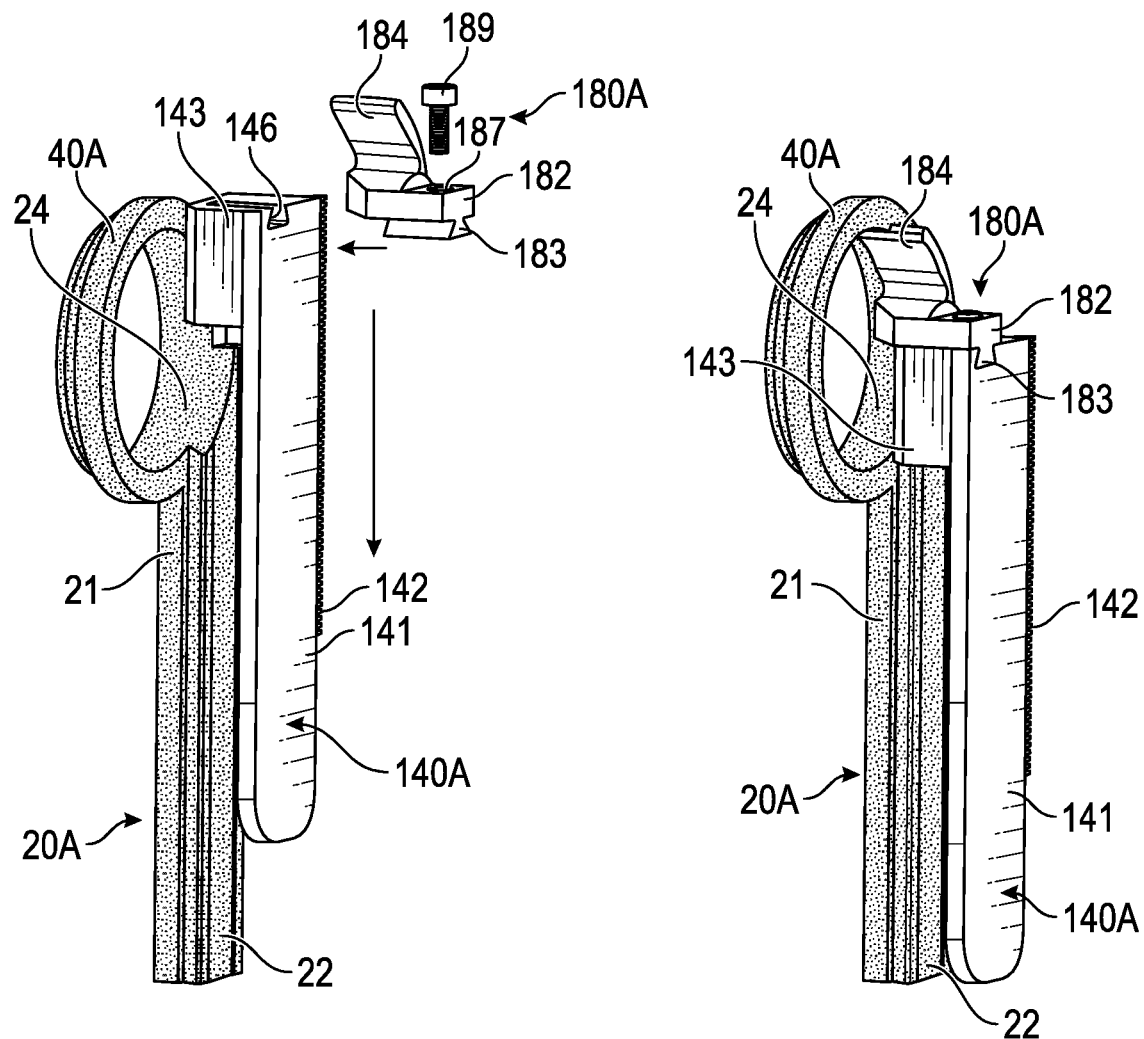
FIG. 10B is a second view in a series of views showing the Z-rack and ring supports of FIGS. 7A-7C and 8A-8D being engaged with an arc support portion of the Leksell frame of FIGS. 1A and 1B.

Referring to FIG. 10B, the Z-rack 140A of the stereotactic coordinate adjuster system 100 is engaged with the arc support member 20A of the stereotactic frame system 10. In particular, the arc shoulder receptacle 144 (FIG. 5) of the Z-rack 140A engages the ring shoulder 24 of the ring 40A, and ring support 180A supports the ring 40A of the arc support member 20A by contacting the interior portion of the ring 40A as shown in FIG. 10B. Z-rack 140A engages with ring support 180 by insertion of the dovetail stabilizer 183 into the ring support receptacle 146 of the Z-rack 140A, shown in FIG. 10E. In addition, ring support 180A may be stabilized by insertion of base screw 189 into screw receptacles 187 and 147. As discussed, rail gripper 145/245 is further tightened against the arc support member 20A, thus allowing the head portion 143 to encapsulate the ring shoulder 24 of the arc support member 20A.

Figure 10C:
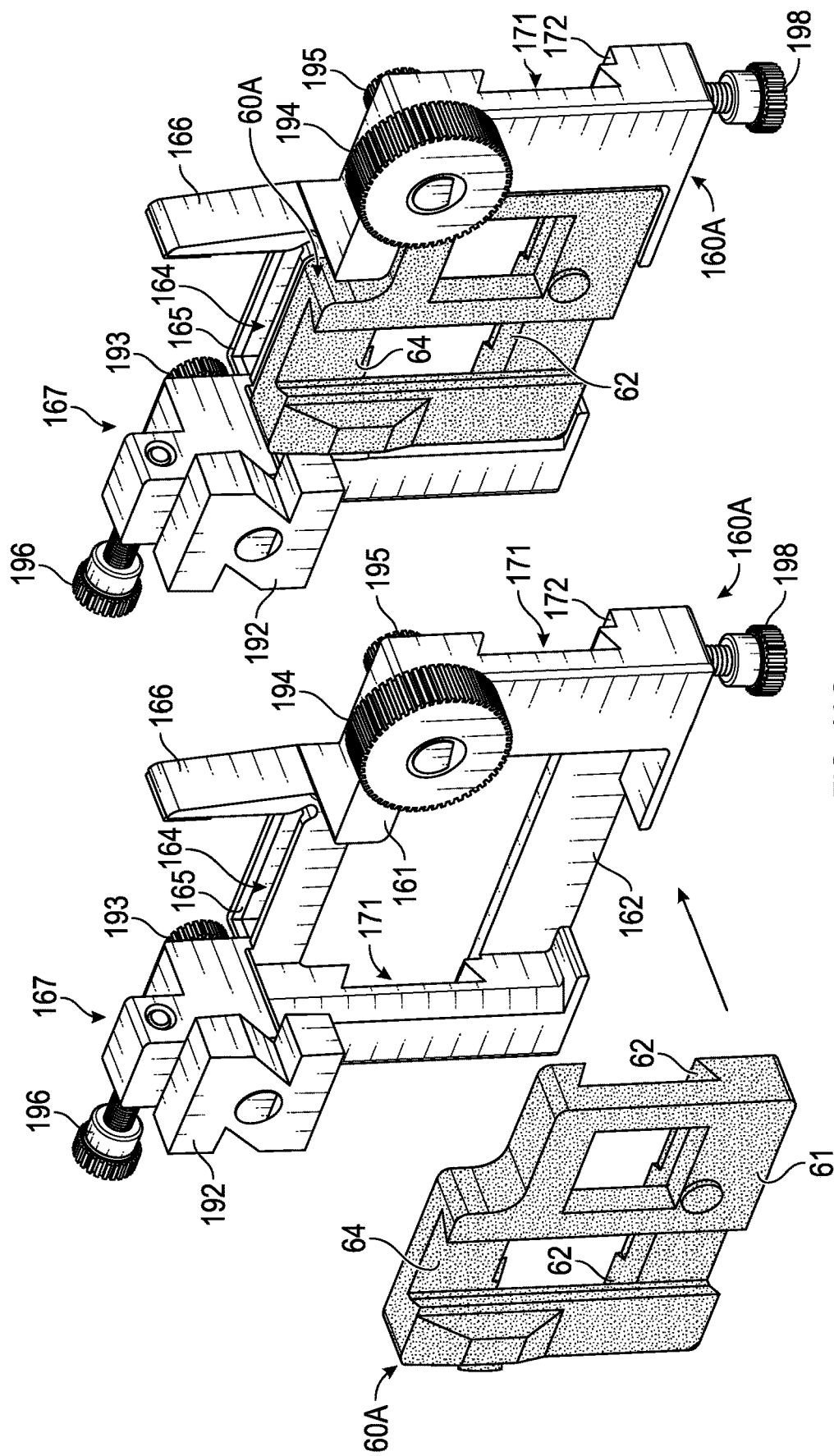
FIG. 10C is a third view in a series of views showing insertion of a slide of the Leksell frame of FIGS. 1A and 1B into the locator of FIGS. 6A-6C.

Referring to FIG. 10C, the locator 160A of the stereotactic coordinate adjuster system 100 is engaged with slide portion 60A of the stereotactic frame system 10. In particular, slide portion 60A is inserted into the locator receptacle 162 of the locator 160A such that the Y-receptacle 62 of the slide portion 60A aligns with the track 171 of the locator 160A.

Figure 10D:
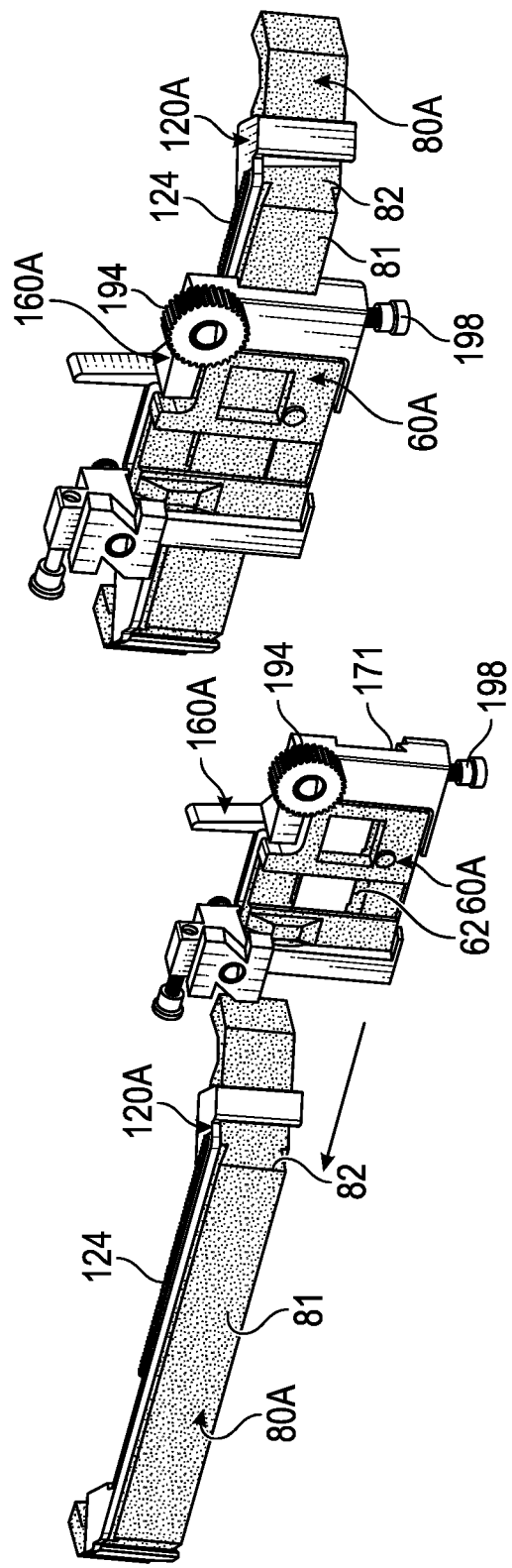
FIG. 10D is a fourth view in a series of views showing alignment and engagement of the locator of FIGS. 6A-6C with the Y-rack and frame portion of FIG. 10A.

Referring to FIG. 10D, the assembled Y-rack 120A and frame portion 80A are engaged with the assembled locator 160A and slide portion 60 by insertion of the dovetail portion 82 into the track 171 of the assembled locator 160A. As a result, the Y-pinion 195 of the locator 160A engages the gear rack 124 of the Y-rack 120A. In some embodiments, the Y-bolt 198 is tightened through the locator 160A against the frame portion 80A such that the positions of the Y-rack 120A and frame portion 80A are held in place.

Figure 10E:
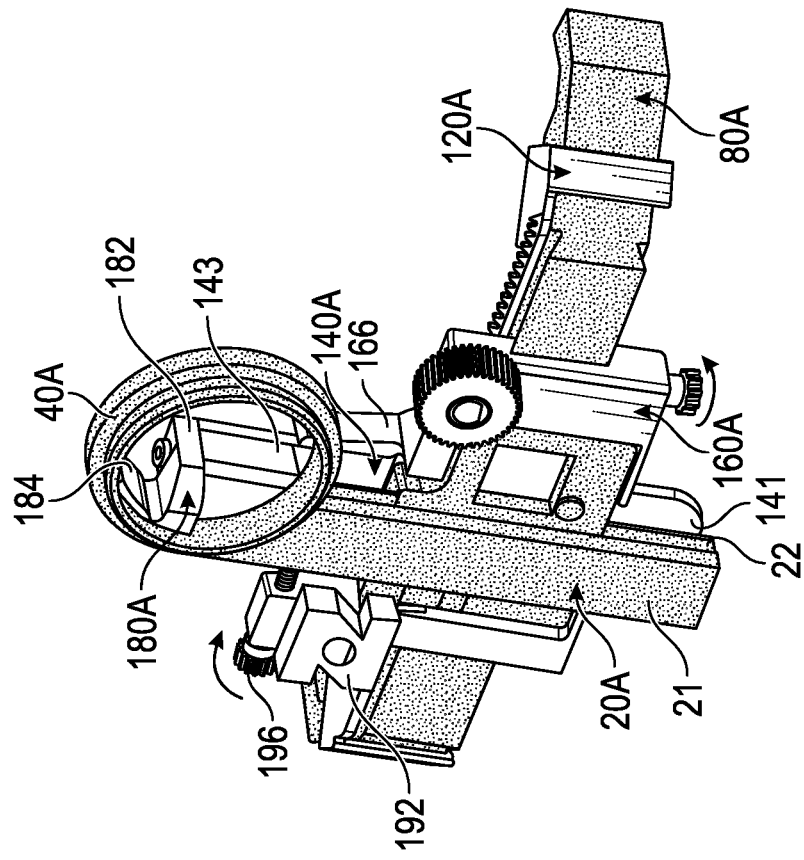
FIG. 10E is a fifth view in a series of views showing insertion of the Z-rack and arc support portion of FIG. 10B into the locator of FIG. 10D.
Figure 10E:
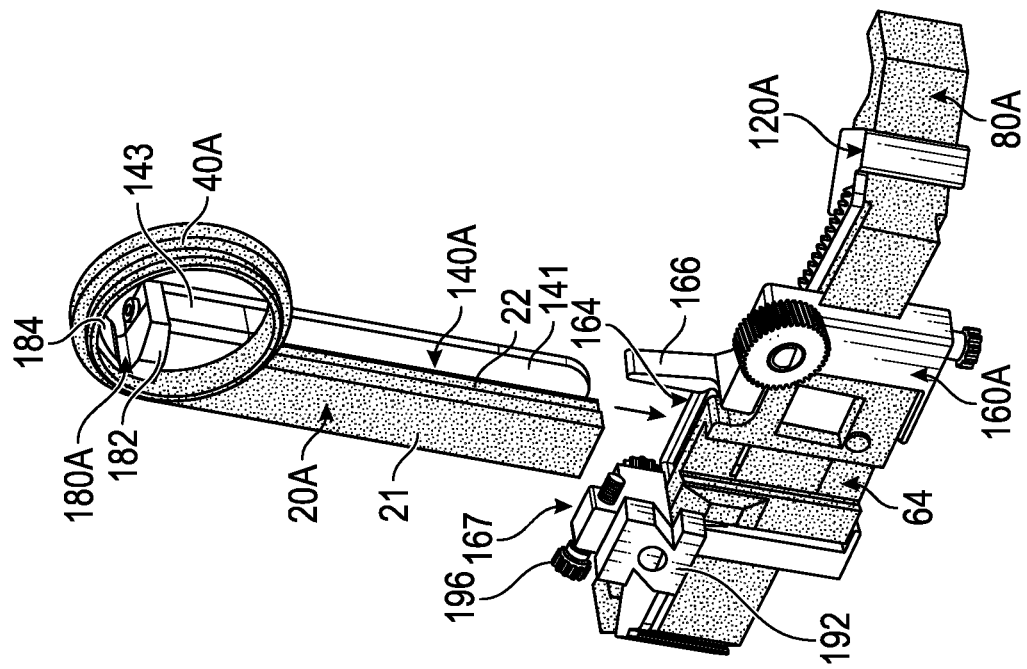

Referring to FIG. 10E, the assembled Z-rack 140A and arc support member 20A are engaged with the assembled locator 160A and slide portion 60A by insertion of the dovetail portion 22 into the Z-receptacle 64 of the slide portion 60A. Simultaneously, the elongated body 141 of the Z-rack 140A is inserted into the Z-rack guide slot 164 of the locator 160A such that the Z-pinion 193 engages the gear rack 142 of the Z-rack 140A. In some embodiments, the Z-bolt 196 is tightened through the locator 160A against the arc support member 20A such that the positions of the Z-rack 120A and arc support member 20A are held in place.

In one method of adjusting the horizontal position of the arc support member 20A of the stereotactic frame system 10 using the stereotactic coordinate adjuster system 100, the Y-bolt 198 is first loosened and the locator 160A moved to the left direction or to the right direction relative to the frame portion 80A and associated Y-rack 120A, depending on the ideal position selected by the practitioner. In some embodiments, this can be done manually for larger movements. Conversely, finer adjustments of the stereotactic frame system 10 can be made by carefully rotating the Y-dial 194 in a clockwise or counterclockwise direction such that the Y-pinion 195 travels in either a left direction or right direction along the gear rack 124 such that the locator 160A, and by association the arc support member 20A, is moved to the desired location along the frame portion 80A. Once an ideal position has been reached, the Y-bolt 198 can be tightened to secure the horizontal location of the arc support member 20A.

Similarly, in one method of adjusting a vertical position of the arc support member 20A of the stereotactic frame system 10 using the stereotactic coordinate adjuster system 100, the Z-bolt 196 is loosened and the arc support member 20A and associated Z-rack 140A are moved either up or down relative to the frame portion 80A and associated Y-rack 120A, depending on the ideal position selected by the practitioner. In some embodiments, this is be done manually for larger movements. Conversely, finer adjustments can be made by carefully rotating the Z-dial 192 in a clockwise or counterclockwise direction such that the Z-pinion 195 lifts or lowers the gear rack 142 such that the arc support member 20A is moved to the desired vertical location relative to the locator 60A. Once the ideal position has been reached, the Z-bolt 196 can be tightened to secure the vertical location of the arc support member 20A.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. A system for fine adjustment of a stereotactic frame system, comprising:
    a stereotactic frame system, including a left portion and a right portion, each of the left and right portions comprising:
        a frame portion defined along a horizontal axis Y;
        an arc support member defined perpendicular to the first frame portion along a vertical axis Z, wherein the arc support member defines a respective ring; and
        a slide portion configured to receive the first frame portion and the arc support member, wherein moving the slide portion along the horizontal axis Y causes the arc support member to be moved along the horizontal axis Y relative to the first frame portion and wherein the arc support member can be lifted or lowered along the vertical axis Z relative to the slide portion;

a stereotactic coordinate adjuster system configured to engage with the stereotactic frame system for fine adjustment of the stereotactic frame system, including a left coordinate adjuster and a right coordinate adjuster, each of the left and right coordinate adjusters comprising:

a locator configured to receive the slide portion of the stereotactic frame system, the locator defining a rectangular body including a vertically oriented first receptacle positioned along a rear portion of the rectangular body, and a horizontally oriented second receptacle positioned along a front portion of the body;

wherein the locator further includes a first pinion and an associated first dial oriented in an X-direction, the first pinion and first dial being associated with the first receptacle;

wherein the locator further includes a second pinion and associated second dial oriented in a Y-direction, the second pinion and second dial being associated with the second receptacle;

a vertically oriented z-rack configured for engagement with the arc support member of the stereotactic frame system and defining a first elongated body and a head portion, wherein the first elongated body defines a first gear rack along a side of the first elongated body, wherein the first gear rack is configured for engagement with the first pinion; and a horizontally oriented y-rack configured for engagement with the frame portion of the stereotactic frame system and defining a second elongated body including a rail portion defining a second gear rack, wherein the second gear rack is configured to engage the second pinion of the locator;

wherein the vertically oriented first receptacle of the locator is configured to receive the vertically oriented z-rack and wherein the horizontally oriented second receptacle of the locator is configured to receive the horizontally oriented y-rack and the frame portion of the stereotactic frame system.

2. The system of claim 1, wherein the head portion of the vertically oriented z-rack includes:

a ring receptacle for receipt of a shoulder defined by the arc support member of the stereotactic frame system along a face of the head portion, wherein the face defines an arcuate recess for receipt of the shoulder;

wherein the ring receptacle further defines a retainer portion configured to apply pressure to a side of the arc support member; and a ring support receptacle defined at a top of the head portion for receipt of the ring support assembly.

3. The system of claim 2, wherein the ring support assembly is in association with the head portion and includes a base and an arcuate lever extending from the base operable for directly engaging and providing support for an interior portion of the ring.

4. The system of claim 3, wherein the base defines a bottom surface and includes a dovetail stabilizer, the dovetail stabilizer being configured for engagement with the receptacle of the head portion.

5. The system of claim 1, wherein the locator and the vertically oriented z-rack are oriented such that as the first dial is operable for rotation in a clockwise direction or a counterclockwise direction, wherein the first pinion is operable for rotation in a clockwise or counterclockwise direction such that the first gear rack and associated head portion of the vertically oriented z-rack is lifted or lowered relative to the locator.

6. The system of claim 1, wherein the locator and the horizontally oriented y-rack are oriented such that as the second dial is operable for rotation in a clockwise direction or a counterclockwise direction, the second pinion is operable for rotation in a clockwise or counterclockwise direction such that the locator is moved in a first horizontal direction or opposite second horizontal direction relative to the second gear rack of the horizontally oriented y-rack.

7. The system of claim 1, the horizontally oriented y-rack comprises a first shoulder capsule defined at a first end of the second elongated body and a second shoulder capsule defined at a second end of the second elongated body, wherein the rail portion is located between the first shoulder capsule and the second shoulder capsule.

8. The system of claim 7, wherein the first shoulder capsule is configured to receive a first shoulder of the frame portion of the stereotactic frame system and wherein the second shoulder capsule is configured to receive a second shoulder of the frame portion of the stereotactic frame system.

9. The system of claim 8, wherein the first shoulder capsule and the second shoulder capsule each include an outer surface clip configured to encapsulate an outer surface of the respective first or second shoulder of the frame portion of the stereotactic frame system.

10. The system of claim 9, wherein each outer surface clip includes a respective tang configured to engage with a respective bottom surface of the first or second shoulder of the frame portion of the stereotactic frame portion.

11. The system of claim 8, wherein the first shoulder capsule and the second shoulder capsule each define an inner surface configured to encapsulate an inner surface of the respective first or second shoulder of the frame portion of the stereotactic frame system.

12. The system of claim 1, wherein the horizontally oriented second receptacle of the locator includes a track, wherein the track includes a first track portion and a second track portion, wherein the first track portion is set apart from the second track portion by a slide receptacle, wherein the slide receptacle defined by the locator is configured to engage a Y-receptacle of the slide portion to collectively define the track.

13. The system of claim 1, wherein the locator further includes a tensioner element configured to engage the vertically oriented z-rack and is operable to push the first gear rack of the vertically oriented z-rack against the first pinion.

14. The system of claim 1, wherein the vertically oriented receptacle of the locator is configured at the rear portion of the locator to receive the first elongated body of the vertically oriented z-rack such that as the arc support member is engaged with the slide portion of the stereotactic frame system, the first elongated body of the vertically oriented z-rack is inserted into the vertically oriented receptacle of the locator and the first pinion engages the first gear rack of the vertically oriented z-rack.

15. A method for fine adjustment of a stereotactic system, comprising:

providing a stereotactic frame system, comprising:

a frame portion defining a first shoulder, a second shoulder, and a first dovetail portion defined between the first shoulder and the second shoulder;

an arc support member defining a ring at a top portion of the arc support member and a ring shoulder defined between the ring and the arc support member, wherein the arc support member defines a second dovetail portion; and
a slide portion configured to receive the first dovetail portion of the frame portion and the second dovetail portion of the arc support member;
providing a stereotactic coordinate adjuster system for engagement with the stereotactic frame system, comprising:
a vertically oriented z-rack defining a head portion and a first elongated body, wherein the first elongated body defines a first gear rack, wherein the vertically oriented z-rack is associated with a ring support assembly, and wherein the vertically oriented z-rack is configured for engagement with the arc support member of the stereotactic frame system;
a horizontally oriented y-rack defining a first shoulder capsule, a second shoulder capsule, and a second gear rack located between the first shoulder capsule and the second shoulder capsule, wherein the horizontally oriented y-rack is configured for engagement with the frame portion of the stereotactic frame system;
a locator defining a slide receptacle configured for engagement with the slide portion of the stereotactic frame system, a horizontally oriented receptacle associated with a first pinion and configured for engagement with the horizontally oriented y-rack, and a vertically oriented receptacle associated with a second pinion and configured for engagement with the vertically oriented z-rack;
engaging the horizontally oriented y-rack of the stereotactic coordinate adjuster system with the frame portion of the stereotactic frame system such that the first shoulder and the second shoulder of the frame portion are encapsulated by the first shoulder capsule and the second shoulder capsule of the horizontally oriented y-rack;
engaging the vertically oriented z-rack and the ring support assembly of the stereotactic coordinate adjuster system with the arc support member of the stereotactic system such that the head portion of the vertically oriented z-rack encapsulates the ring shoulder of the arc support member of the stereotactic system and the ring support assembly contacts the ring of the arc support member;
engaging the locator of the stereotactic coordinate adjuster system with the slide portion of the stereotactic frame system such that the slide portion is encapsulated by the slide receptacle of the locator;
inserting the first dovetail portion of the frame portion of the stereotactic system into the horizontally oriented receptacle of the locator such that the first pinion of the locator engages with the first gear rack of the vertically oriented z-rack; and
inserting the second dovetail portion of the arc support member of the stereotactic system into the vertically oriented receptacle of the locator such that the second pinion of the locator engages with the second gear rack of the horizontally oriented z-rack.

16. The method of claim 15, further comprising:
engaging the ring support assembly with the vertically oriented z-rack by insertion of a dovetail stabilizer of the ring support assembly into a receptacle defined at a top of the head portion of the vertically oriented z-rack.

17. The method of claim 15, further comprising:
adjusting a vertical position of the arc support member relative to the frame portion of the stereotactic frame by rotating a first dial operatively associated with the first pinion of the locator in a clockwise or counterclockwise rotational direction such that the first gear rack of the vertically oriented z-rack and the associated arc support member are lifted or lowered relative to the locator.

18. The method of claim 15, further comprising:
adjusting a horizontal position of the arc support member relative to the frame portion of the stereotactic frame by rotating a second dial operatively associated with the second pinion of the locator in a clockwise or counterclockwise rotational direction such that the second gear rack of the horizontally oriented y-rack and the associated frame portion are moved left or right relative to the locator.

19. The method of claim 15, further comprising:
securing a vertical position of the arc support member relative to the frame portion of the stereotactic frame by tightening a first bolt through the locator and against the arc support member; and
securing a horizontal position of the arc support member relative to the frame portion of the stereotactic frame by tightening a second bolt through the locator and against the frame portion.

20. A stereotactic coordinate adjuster system, comprising:
a left coordinate adjuster and a right coordinate adjuster, each of the left and right coordinate adjusters comprising:
a locator, the locator defining a rectangular body including a vertically oriented first receptacle positioned along a rear portion of the rectangular body, and a horizontally oriented second receptacle positioned along a front portion of the body;
wherein the locator further includes a first pinion and an associated first dial oriented in an X-direction, the first pinion and first dial being associated with the first receptacle;
wherein the locator further includes a second pinion and associated second dial oriented in a Y-direction, the second pinion and second dial being associated with the second receptacle;
a vertically oriented z-rack defining a first elongated body and a head portion, wherein the first elongated body defines a first gear rack along a side of the first elongated body, wherein the first gear rack is configured for engagement with the first pinion; and
a horizontally oriented y-rack defining a second elongated body including a rail portion defining a second gear rack, wherein the second gear rack is configured to engage the second pinion of the locator;
wherein the vertically oriented first receptacle of the locator is configured to receive the vertically oriented z-rack and wherein the horizontally oriented second receptacle of the locator is configured to receive the horizontally oriented y-rack.

21. The system of claim 20, wherein the head portion of the vertically oriented z-rack includes:
a ring receptacle defined along a face of the head portion, wherein the face defines an arcuate recess;
wherein the ring receptacle further defines a retainer portion; and
a ring support receptacle defined at a top of the head portion.

22. The system of claim 21, wherein the ring support assembly is in association with the head portion and includes a base and an arcuate lever extending from the base.

23. The system of claim 22, wherein the base defines a bottom surface and includes a dovetail stabilizer, the dovetail stabilizer being configured for engagement with the receptacle of the head portion.

24. The system of claim 20, wherein the locator and the vertically oriented z-rack are oriented such that as the first dial is operable for rotation in a clockwise direction or a counterclockwise direction, wherein the first pinion is operable for rotation in a clockwise or counterclockwise direction such that the first gear rack and associated head portion of the vertically oriented z-rack is lifted or lowered relative to the locator.

25. The system of claim 20, wherein the locator and the horizontally oriented y-rack are oriented such that as the second dial is operable for rotation in a clockwise direction or a counterclockwise direction, the second pinion is operable for rotation in a clockwise or counterclockwise direction such that the locator is moved in a first horizontal direction or opposite second horizontal direction relative to the second gear rack of the horizontally oriented y-rack.

26. The system of claim 20, the horizontally oriented y-rack comprises a first shoulder capsule defined at a first end of the second elongated body and a second shoulder capsule defined at a second end of the second elongated body, wherein the rail portion is located between the first shoulder capsule and the second shoulder capsule.

27. The system of claim 26, wherein the first shoulder capsule and the second shoulder capsule each include an outer surface clip.

28. The system of claim 27, wherein each outer surface clip includes a respective tang.

29. The system of claim 27, wherein the first shoulder capsule and the second shoulder capsule each define an inner surface tab.

30. The system of claim 20, wherein the horizontally oriented second receptacle of the locator includes a track, wherein the track includes a first track portion and a second track portion, wherein the first track portion is set apart from the second track portion.

31. The system of claim 20, wherein the locator further includes a tensioner element configured to engage the vertically oriented z-rack and is operable to push the first gear rack of the vertically oriented z-rack against the first pinion.

32. The system of claim 20, wherein the vertically oriented receptacle of the locator is configured at the rear portion of the locator to receive the first elongated body of the vertically oriented z-rack such that the first elongated body of the vertically oriented z-rack is operable to be inserted into the vertically oriented receptacle of the locator and the first pinion engages the first gear rack of the vertically oriented z-rack.

* * * * *